United States Patent
Schuelke et al.

(10) Patent No.: US 12,067,652 B2
(45) Date of Patent: Aug. 20, 2024

(54) CORRECTION OF MAGNETIC RESONANCE IMAGES USING MULTIPLE MAGNETIC RESONANCE IMAGING SYSTEM CONFIGURATIONS

(71) Applicant: KONINKLIJKE PHILIPS N.V., Eindhoven (NL)

(72) Inventors: Christophe Michael Jean Schuelke, Hamburg (DE); Karsten Sommer, Hamburg (DE); George Randall Duensing, Hamburg (DE); Peter Boernert, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 86 days.

(21) Appl. No.: 17/923,617

(22) PCT Filed: Apr. 21, 2021

(86) PCT No.: PCT/EP2021/060286
§ 371 (c)(1),
(2) Date: Nov. 7, 2022

(87) PCT Pub. No.: WO2021/228515
PCT Pub. Date: Nov. 18, 2021

(65) Prior Publication Data
US 2023/0186532 A1  Jun. 15, 2023

Related U.S. Application Data

(60) Provisional application No. 63/022,925, filed on May 11, 2020.

(30) Foreign Application Priority Data

May 28, 2020  (EP) .................................... 20176989

(51) Int. Cl.
*G06T 11/00* (2006.01)
*G01R 33/54* (2006.01)
(Continued)

(52) U.S. Cl.
CPC .......... *G06T 11/005* (2013.01); *G01R 33/543* (2013.01); *G01R 33/5608* (2013.01);
(Continued)

(58) Field of Classification Search
CPC ................ G01R 33/543; G01R 33/565; G01R 33/5608; G06T 11/005; G06T 11/006; G06T 2211/424
See application file for complete search history.

(56) References Cited

U.S. PATENT DOCUMENTS 11,756,160 B2 *  9/2023  Park ....................... G06N 3/048
                                                          382/276
2012/0189183 A1   7/2012  Xue et al.
(Continued)

FOREIGN PATENT DOCUMENTS

WO    2007124450 A2   11/2007
WO     201009348 A2    1/2010
(Continued)

OTHER PUBLICATIONS

Jiang et al "Compressed Sensing MRI Reconstruction Based on Generative Adversarial Nets" 2018 Int. Conf. on Computer Science and Software Engineering, (CSSE 2018).
(Continued)

*Primary Examiner* — Gregory H Curran

(57) ABSTRACT

Disclosed herein is a medical system (100, 300) comprising a memory (110) storing machine executable instructions (120) and an image generating neural network (122). The image generating neural network is configured for outputting synthetic magnetic resonance image data (128) in
(Continued)

response to receiving reference magnetic resonance image data (126) as input. The synthetic magnetic resonance image data is a simulation of magnetic resonance image data acquired according to a first configuration of a magnetic resonance imaging system when the reference magnetic resonance image data is acquired according to a second configuration of the magnetic resonance imaging system. Execution of the machine executable instructions causes a computational system (106) to: receive (200) measured k-space data (124) acquired according to the first configuration of the magnetic resonance imaging system; receive (202) the reference magnetic resonance image data; receive (204) the synthetic magnetic resonance image data by inputting the reference magnetic resonance image data into the image generating neural network; and reconstruct (206) corrected magnetic resonance image data (132) from the measured k-space data and the synthetic magnetic resonance image data.

15 Claims, 15 Drawing Sheets

(51) Int. Cl.
 *G01R 33/56* (2006.01)
 *G01R 33/565* (2006.01)
(52) U.S. Cl.
 CPC .......... *G01R 33/565* (2013.01); *G06T 11/006* (2013.01); *G06T 2211/424* (2013.01)

(56) References Cited

U.S. PATENT DOCUMENTS

| | | | |
|---|---|---|---|
| 2013/0088225 A1* | 4/2013 | Weller | G01R 33/5611 324/322 |
| 2016/0274209 A1 | 9/2016 | Dannels | |
| 2017/0309019 A1 | 10/2017 | Knoll et al. | |
| 2019/0035078 A1 | 1/2019 | Zaharchuk et al. | |
| 2019/0172230 A1 | 6/2019 | Mailhe et al. | |
| 2019/0347772 A1 | 11/2019 | Zhang et al. | |
| 2019/0377047 A1 | 12/2019 | Chen et al. | |
| 2020/0209331 A1* | 7/2020 | Meineke | G01R 33/565 |

FOREIGN PATENT DOCUMENTS

| | | |
|---|---|---|
| WO | 2015197366 A1 | 12/2015 |
| WO | 2019086284 A1 | 5/2019 |
| WO | 2019224800 A1 | 11/2019 |

OTHER PUBLICATIONS

Zeng et al "A Very Deep Densely Connected Network for Compressed Sensing MRI" IEEE Access, Jun. 1, 2019.
Lei Xiang et al "Deep Learning Based Multi-Modal Fusion for Fast MR Reconstruction" IEEE Transactions on Biomedical Engineering, vol. 66, No. 7 Jul. 1, 2019. p. 2105-2114.
Sun et al "A Deep Information Sharing Network for Multi-contrast Compressed Sensing MRI Reconstruction" Apr. 10, 2018, Cornell University Library.
Knoll et al "Adapted Random Sampling Patterns for Accelerated MRI" Magnetic Resonace Materials in Physics . . . , vol. 24, No. 1 Jan. 7, 2011 p. 43-50.
Mardani et al "Deep Generative Adversarial Neural Networks for Compressive Sensing MRI" IEEE Transactions on Medical Imaging, vol. 38, No. 1 Jan. 2019.
International Search Report and Written Opinion from PCT/EP2021/060286 dated Jun. 16, 2021.
Ehrhardt, Matthias J., and Marta M. Betcke. "Multicontrast MRI reconstruction with structure-guided total variation." SIAM Journal on Imaging Sciences 9.3 (2016): 1084-1106.
Bilgic, Berkin, Vivek K. Goyal, and Elfar Adalsteinsson. "Multicontrast reconstruction with Bayesian compressed sensing." Magnetic resonance in medicine 66.6 (2011): 1601-1615.
Chatnuntawech, Itthi, et al. "Vectorial total generalized variation for accelerated multi-channel multi-contrast MRI." Magnetic resonance imaging 34.8 (2016): 1161-1170.
Zhu, Jun-Yan, et al. "Unpaired image-to-image translation using cycle-consistent adversarial networks." Proceedings of the IEEE international conference on computer vision. 2017.
Karras, Tero, Samuli Laine, and Timo Aila. "A style-based generator architecture for generative adversarial networks." Proceedings of the IEEE Conference on Computer Vision and Pattern Recognition. 2019.
Ronneberger, O., Fischer, P., Brox, T. U-net: Convolutional networks for biomedical image segmentation. In International Conference on Medical image computing and computer-assisted intervention, pp. 234-241, 2015.
Brosch T, Saalbach A. Foveal Fully Convolutional Nets for Multi-Organ Segmentation. In Proceedings of the SPIE, vol. 10574, 2018.
Mohammed, A., et al. Y-Net: a deep Convolutional Neural Network for Polyp Detection. arXiv preprint arXiv:1806.01907, 2018.
Zaitsev M et al. Motion artifacts in MRI: a complex problem with many partial solutions. Journal of Magnetic Resonance Imaging 42(4):887-901, 2015.
McGee KP et al. Image metric-based correction (autocorrection) of motion effects: analysis of image metrics. Journal of Magnetic Resonance Imaging 11(2):174-181, 2000.
Huang X, Belongie S. Arbitrary Style Transfer in Real-time with Adaptive Instance Normalization, arXiv:1703.06868v2, 2017.

* cited by examiner

CORRECTION OF MAGNETIC RESONANCE IMAGES USING MULTIPLE MAGNETIC RESONANCE IMAGING SYSTEM CONFIGURATIONS

CROSS REFERENCE TO RELATED APPLICATIONS

This application is a U.S. national phase application of International Application No. PCT/EP2021/060286 filed Apr. 21, 2021, which claims the benefit of EP Application Serial No. 20176989.0 filed May 28, 2020 and U.S. Provisional Application 63/022,925 filed May 11, 2020 and is incorporated herein by reference.

FIELD OF THE INVENTION

The invention relates to Magnetic Resonance Imaging, in particular to the reduction of artifacts in magnetic resonance images.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Various quantities or properties of the subject can be measured spatially using MRI. For example, various electrical and tissue properties of a subject can be investigated using MM. A difficulty in MM is that it may take several minutes to acquire sufficient k-space data to reconstruct the magnetic resonance image. Motion of the subject or the reception of spurious RF signals may cause artifacts or corrupt the magnetic resonance image.

United States patent application publication US20190377047A1 discloses the use of a deep learning to train an image-to-image neural network to generate an image with reduced artifacts for a magnetic resonance imaging system. The image-to-image network may be applied in real time. To handle a range of different imaging situations, the image-to-image network may (a) use an auxiliary map as an input with the MR data from the patient, (b) use sequence metadata as a controller of the encoder of the image-to-image network, and/or (c) be trained to generate contrast invariant features in the encoder using a discriminator that receives encoder features.

The international application WO2019/224800 concerns simulating and constructing actual MRI image in a second modality form a source MM image taken in a first modality.

SUMMARY OF THE INVENTION

The invention provides for a medical system, a computer program, and a magnetic resonance imaging system in the independent claims. Embodiments are given in the dependent claims. Accordingly, the medical system comprises a memory storing machine executable instructions and access to an image generating neural network. The image generating neural network may be incorporated in the medical system or the medical system may be configured to control to have access through a datalink to the image generating neural network that may be installed remotely. The image generating neural network is configured for outputting synthetic magnetic resonance image data in response to receiving reference magnetic resonance image data as input, and the image generating neural network is configured to generate the synthetic magnetic resonance image data as a simulation of magnetic resonance image data acquired according to a first configuration of a magnetic resonance imaging system when the reference magnetic resonance image data is acquired according to a second configuration of the magnetic resonance imaging system. A computational system is configured for controlling the medical system, wherein execution of the machine executable instructions causes the computational system to:

access measured k-space data acquired according to the first configuration of the magnetic resonance imaging system, wherein the measured k-space data is descriptive of a region of interest of a subject;

access the reference magnetic resonance image data, wherein the reference magnetic resonance image data is descriptive of the region of interest of the subject;

generate access to the synthetic magnetic resonance image data by inputting the reference magnetic resonance image data into the image generating neural network; and arrange to reconstruct corrected magnetic resonance image data from the measured k-space data and the synthetic magnetic resonance image data.

The access to the measured k-space data and the reference magnetic resonance image data may be implemented in that the medical system receives these data and is enabled to forward to input into the image generating neural network that may be remote from or incorporated in the medical system. The access to the measured k-space data and the reference magnetic resonance image data may also be implemented in the these data are remotely controlled to be input to and output from the image generating neural network, respectively. The generation of access to the synthetic magnetic resonance image data may be from a remotely located image generating neural network by remotely controlling synthetic magnetic resonance image data to be applied to reconstruction software. The generation of access may also be implemented in that the medical system receives the synthetic magnetic resonance image data and forwards these data to reconstruction software or applies these data to reconstruction software incorporated in the medical system.

Subject motion, spurious RF signals, or other failures can cause artifacts or corrupt a magnetic resonance image. Embodiments may provide for a means of reducing artifacts or image corruption and or to accelerate image acquisition. An image generating neural network may be trained to receive reference magnetic resonance image data that was acquired using a second configuration of a magnetic resonance imaging system and output synthetic magnetic resonance image data. The synthetic magnetic resonance image data is a simulation of magnetic resonance image data acquired for a first configuration of the magnetic resonance imaging system.

The synthetic magnetic resonance image data can then be used to improve the reconstruction of a corrected magnetic resonance image from measured k-space data acquired using the first configuration of the magnetic resonance imaging system. The synthetic magnetic resonance image data can in one example provide prior knowledge which can be used in a regularization term during a reconstruction. In another example the synthetic magnetic resonance image data can be used to calculate synthetic k-space data which can, for example, be used to modify, supplement, correct, or replace portions of the measured k-space data.

The magnetic resonance imaging system is configured to arrange for reconstruction of the set of magnetic resonance images from the echo signals in that reconstruction software is installed in the magnetic resonance examination system's computational system or in that the computational system has access to a remote reconstruction facility. The reconstruction software may be installed on a remote server, e.g. in the healthcare institution where the magnetic resonance imaging system is installed, or even be accessible to a data-network in that the reconstruction software may be available in 'the cloud', In these remote configurations the computational system is equipped with functionality to arrange for reconstruction of the set of magnetic resonance images at the remotely located reconstruction function. Moreover, reconstruction of the magnetic resonance image may be done by way of machine learning, for example by a trained neural network that may be incorporated ion the computational system or may be accessible from a remote location and forward to reconstruction.

In one aspect the invention provides for a medical system that comprises a memory storing machine-executable instructions and an image generating neural network. The image generating neural network is configured for outputting a synthetic magnetic resonance image in response to receiving a reference magnetic resonance image data as input. The image generating neural network is configured to generate the synthetic magnetic resonance image as a simulation of a magnetic resonance image data acquired according to a first configuration of a magnetic resonance imaging system when the reference magnetic resonance image data is acquired according to a second configuration of the magnetic resonance imaging system.

In other words, the image generating neural network takes a reference magnetic resonance image data that is acquired according to a second configuration and then generates a synthetic magnetic resonance image that simulates a magnetic resonance image acquired according to a first configuration of the magnetic resonance imaging system. The first and second configuration could for example be a difference in the type of pulse sequence used to control the magnetic resonance imaging system to generate a specific MR contrast. In other examples the differences between the first and second configuration could be a change in the configuration of a similar pulse sequence. For example, the TE or TR values may be changed. In other example the same pulse sequence could be used with a different resolution. Often times even using different magnetic resonance imaging protocols much of the data is redundant. This enables a synthetic magnetic resonance image data to be output with a fairly high degree of accuracy.

The image generating neural network may be trained in a straight forward way. A magnetic resonance imaging system may for example be used to acquire a training image using the second configuration of the magnetic resonance image and then before or after acquiring a ground truth image that is acquired with the first configuration of the magnetic resonance imaging system. Doing this once provides one pair of training data. This process may be repeated with different subjects and different configurations as desired. This training data may then for example be used using a back propagation or deep learning algorithm to train the image generating neural network.

The medical system further comprises a computational system that is configured for controlling the medical system. The computational system may take different forms in different examples. In one example the computational system may be a workstation, for example those used by a radiologist. In other examples the computational system may be a remote computational system or a cloud computing system that provides image processing surfaces. In another example the computational system may be a computational system that controls the operation and function of a magnetic resonance imaging system.

Execution of the machine-executable instructions causes the computational system to receive measured k-space data acquired according to the first configuration of the magnetic resonance imaging system. The measured k-space data is descriptive of a region of interest of a subject. Execution of the machine-executable instructions further causes the computational system to receive the reference magnetic resonance image data. The reference magnetic resonance image data is descriptive of the region of interest of the subject. Execution of the machine-executable instructions further causes the computational system to receive the synthetic magnetic resonance image data by inputting the reference magnetic resonance image data into the image generating neural network.

Then finally, execution of the machine-executable instructions causes the computational system to reconstruct the corrected magnetic resonance image data from the measured k-space data and the synthetic magnetic resonance image. The synthetic magnetic resonance image matches the first configuration which was used to acquire the measured k-space data. The synthetic magnetic resonance image may therefore be used to aid in the reconstruction of the corrected magnetic resonance image data.

The magnetic resonance image data as used herein encompasses data which may be used to render or construct one or more magnetic resonance images. For example, the reference magnetic resonance image data may in one example be one or more magnetic resonance images and may in some other examples even be averaged magnetic resonance images. In another example the reference magnetic resonance image data may be an image or mapping generated from a magnetic resonance fingerprinting protocol. Likewise, the synthetic magnetic resonance image data may take different formats in different examples. The synthetic magnetic resonance image data may be data for constructing one or more magnetic resonance images, it may be a three-dimensional magnetic resonance imaging mapping or image dataset. The synthetic magnetic resonance image data may also be the result of a different magnetic resonance fingerprint protocol.

In some examples the reference magnetic resonance image data is a single magnetic resonance image or image data set.

In other examples the reference magnetic resonance image data comprises multiple magnetic resonance images. In some cases, these multiple magnetic resonance images have been acquired using multiple configurations or contrasts. In this case the second configuration of the magnetic resonance imaging system is a collection or bundle of configurations having one configuration for each image or image data set that makes up the reference magnetic resonance imaging data. As a concrete example, three or four or maybe even more magnetic resonance images acquired for different contrasts are grouped together to form the reference magnetic resonance image data.

In another embodiment the image generating neural network is configured for receiving the reference magnetic resonance image data according to a predetermined image format. For example, this could be the format of the images used to train the image generating neural network. Execution of the machine-executable instructions further causes the computational system to convert the reference magnetic resonance image data to the predetermined image format before inputting the reference magnetic resonance image data into the image generating neural network. For example, the size of the region of interest and the voxels may be modified by using standard image transformation techniques. Execution of the machine-executable instructions further causes the computational system to spatially match the synthetic magnetic resonance image data to the measured k-space data before reconstructing the corrected magnetic resonance image data. This could also include modifying the view in the image as well as the positioning of the image. These basic image transformation techniques may be used to format the synthetic magnetic resonance image data so that it matches the first configuration of the magnetic resonance imaging system.

For example, the image generating neural network may be configured to output the synthetic magnetic resonance image according to a predetermined output format. The computational system may adapt this predetermined output format so that it matches the first configuration of the magnetic resonance imaging system.

In another embodiment the measured k-space data and the synthetic magnetic resonance image data are spatially matched. This may for example enable a better comparison of the k-space data.

In some examples the image generating neural network may have an input vector which specifies the first configuration of the magnetic resonance imaging system and the second configuration of the magnetic resonance imaging system. In this case the neural network could automatically adapt the reference magnetic resonance image data and the synthetic magnetic resonance image data. However, this would require a larger amount of training for the image generating neural network.

In another embodiment the synthetic magnetic resonance image data provides prior knowledge during the reconstruction of the corrected magnetic resonance image data. Gross structures such as the location of organs or other anatomical structures may be present in the synthetic magnetic resonance image data. This for example may be useful in replacing or modifying various parts of the measured k-space data. The synthetic magnetic resonance image data may also for example be used as a regularization term during reconstruction to improve the quality of the corrected magnetic resonance image data.

In another embodiment execution of the machine-executable instructions further causes the computational system to reconstruct synthetic k-space data from the synthetic magnetic resonance image data. The measured k-space data is divided into groups of k-space data. The corrected magnetic resonance image data is reconstructed using the synthetic k-space data to modify at least a portion of the groups of the k-space data. Standard techniques may be used to go from image space of the synthetic magnetic resonance image data back to k-space data. The first configuration of the magnetic resonance imaging system may for example be used to calculate backwards to simulate what the k-space data would be like if it were used to produce the synthetic magnetic resonance image data.

For example, in a parallel imaging technique the coil sensitivities may be used to even generate simulated images for each coil or acquisition channel, which may then be used in turn to simulate the acquired k-space data from individual coils or channels. This may be beneficial because it may enable the compensation for noise or other errors when acquiring the measured k-space data.

In another embodiment execution of the machine-executable instructions further causes the computational system to use the synthetic k-space data to determine a rigid body transformation of one or more of the groups of k-space data. Execution of the machine-executable instructions further causes the computational system to perform a phase and amplitude correction of the one or more groups of k-space data using the rigid body transformation. This embodiment may be beneficial because it may provide for a straight forward way of reducing the effects of rigid body motion by a subject.

In another embodiment execution of the machine-executable instructions further causes the computational system to use the synthetic k-space data to determine a configuration for a pre-defined motion model. Execution of the machine-executable instructions further causes the computational system to perform a correction of the one or more of the groups of k-space data using the pre-defined motion model. For example, there may be a motion model which may be used to describe affine and/or non-rigid transformations or movement of the subject. This pre-defined motion model may be used to define how the k-space data is modified as the subject moves according to this pre-defined motion model. This may be beneficial because it may enable the correction of the measured k-space data.

In another embodiment the pre-defined motion model is configured to provide a transformation of the synthetic k-space data equivalent to an affine or elastic transformation in image space.

In another embodiment execution of the machine-executable instructions further causes the computational system to detect at least one incomplete k-space data sampling region in the measured k-space data. For example, some of the measured k-space data may be incomplete, corrupted or missing. Execution of the machine-executable instructions further causes the computational system to fill the incomplete k-space sampling region in the measured k-space data with the synthetic k-space data. This may be beneficial because it may improve the quality or enable the use of measured k-space data which would otherwise have to be discarded and reacquired. One situation where this may be beneficial is where the motion of the subject is monitored using a navigator or an external motion measurement system such as a camera or respiration belt. This may enable the automatic detection of k-space data that is corrupted. Once the corrupted k-space data is discarded then the incomplete k-space sampling regions can be filled with the synthetic k-space data.

In another embodiment execution of the machine-executable instructions further causes the computational system to receive a motion signal descriptive of motion of the subject. Execution of the machine-executable instructions further causes the computational system to reconstruct the corrected magnetic resonance image data using the groups of k-space data which have a motion signal within a predetermined range. In this example there may be a motion signal which is provided. This for example could be provided from a magnetic resonance navigator or a system which measures the position of the subject or the change of the motion. For example, respirator belts and cameras may be used. The motion signal is essentially then used to gate which of the k-space data is used.

In another embodiment execution of the machine-executable instructions further causes the computational system to calculate the motion signal as a synthetic motion signal by comparing the synthetic k-space data to each of the groups of k-space data. For example, each of the groups of k-space data may be compared directly to the synthetic k-space data and a fitting may be performed. This may equate to a phase and/or amplitude change of sample points. This may enable the calculation of a motion signal which may be equivalent to a navigator. This may enable the gating of which of the k-space data is used for a particular motion signal. This for example may be useful in producing cardiac phase or breathing phase magnetic resonance images.

The synthetic motion signal may for example be calculated either in k-space or in image space depending upon how large the groups of k-space data are.

In another embodiment the memory further contains an image quality evaluation module configured for outputting an image quality metric. Execution of the machine-executable instructions further causes the computational system to generate multiple k-space datasets by systematically replacing combinations of the groups of k-space data with portions of the synthetic k-space data. Execution of the machine-executable instructions further causes the computational system to generate multiple trial magnetic resonance image data by reconstructing each of the multiple k-space datasets. Execution of the machine-executable instructions further causes the computational system to select the corrected magnetic resonance image data from the multiple trial magnetic resonance image data by optimizing the image quality metric output of the image quality evaluation module.

For example, in executing this algorithm it may for example be decided how many portions of the synthetic k-space data may be used to replace groups of the k-space data. The iterative algorithm can go through and then systematically replace all or many combinations for the optimization process. This embodiment may be beneficial because it may for example enable the correction of data corrupted by noise, spurious signals, or complex involuntary motion when there would be no other way of correcting it.

In another embodiment the image quality metric is determined by using a registration between the synthetic magnetic resonance image data and one of the multiple trial magnetic resonance image data. The synthetic magnetic resonance image data should be similar or very close to the format of what the desired corrected magnetic resonance image data should be. Standard registration techniques may be used to calculate a registration or mapping between the two sets of image data. This metric may then be used to provide the image quality metric. For example, it may measure a similarity between the position of various anatomical landmarks.

In another embodiment the image quality metric is determined using the output from a trained neural network that outputs the image quality metric in response to inputting one of the multiple trial magnetic resonance images. For example, the trained neural network may be trained by taking complete sets of magnetic resonance imaging data and then corrupting or causing fake motion artifacts within this data. This may then be used to assign a classification or metric which can be used for the optimization process.

In another embodiment the image quality metric is determined by calculating a total image gradient of each of the multiple trial magnetic resonance images.

In another embodiment the image quality metric is determined by calculating an image entropy of each of the multiple trial magnetic resonance images.

In another embodiment execution of the machine-executable instructions further causes the computational system to reconstruct multiple corrected magnetic resonance image data. Execution of the machine-executable instructions further causes the computational system to perform any one of the following: to provide the corrected magnetic resonance image data as an average of the multiple corrected magnetic resonance image data and provide the corrected magnetic resonance image as a selection of the multiple corrected magnetic resonance images. For example, one or more of the above-mentioned methods may be used to produce the corrected magnetic resonance image data. To provide a better estimate these images may all be averaged.

In another embodiment the reconstruction of the corrected magnetic resonance image data from the measured k-space data and the synthetic magnetic resonance image is formulated as an optimization problem that assigns weighting factors to each of the groups of k-space data. Execution of the machine-executable instructions further causes the computational system to identify at least one corrupted group of k-space data selected from the groups of k-space data. This identification may be performed in different ways. In some instances, an external navigator or other signal may be used to identify the corrupted k-space data. In other examples the corrupted k-space data may be identified by comparing it to the synthetic k-space data.

Execution of the machine-executable instructions further causes the computational system to correct the at least one corrupted group of k-space data using the synthetic k-space data. Execution of the machine-executable instructions further causes the computational system to assign the weighting factors for each of the groups of k-space data. The at least one corrupted group of k-space data is assigned a reduced value weighting factor. This may be beneficial because then in the reconstruction the measured k-space data which is remaining is given a higher weighting for the reconstruction of the corrected magnetic resonance image. Assigning the reduced value weighting factor to the corrupted group of k-space data which has been corrected enables it to participate in the reconstruction of the corrected magnetic resonance image but it has less of an effect.

In another embodiment the at least one corrupted group of k-space data is selected from the group of k-space data is detected by using any one of the following: an external navigator signal, detecting missing k-space data, or by a comparison with the synthetic k-space data, and combinations thereof.

In another embodiment the correction of the at least one corrupted group of k-space data using the synthetic k-space data is performed using any one of the following: by replacing the at least one corrupted group of k-space data with the synthetic k-space data, modifying or shifting the at least one corrupted group of k-space data, appending the synthetic k-space data to the at least one corrupted group of k-space data, and combinations thereof.

The above embodiments describe a soft gating process. This may be a data consistency term containing weighting factors that reflecting how much of each measurement is trusted. The weights can be for example any positive number. A gating process uses weights that are either 0 or 1, which is one possibility. One could also replace that description by a more general soft gating formulation where the weighting factor w is a positive number that depends on the value of the navigator signal.

In another embodiment the corrected magnetic resonance image data is reconstructed according to a compressed sensing image reconstruction algorithm. This embodiment may be beneficial because the use of the synthetic magnetic resonance image may reduce the amount of data needed to be sampled to reconstruct the corrected magnetic resonance image data.

In another embodiment the compressed sensing image reconstruction algorithm is an iterative algorithm that generates an intermediate magnetic resonance image repeatedly.

The compressed sensing image reconstruction algorithm comprises denoising the intermediate magnetic resonance image using the synthetic magnetic resonance image data.

In another embodiment the compressed sensing image reconstruction algorithm is configured to generate the intermediate magnetic resonance image by solving an optimization problem. The optimization problem includes a regularization term. The regularization term is a function of the synthetic magnetic resonance image data and performs the denoising of the intermediate magnetic resonance image using the synthetic magnetic resonance image data.

In another embodiment the memory further contains an image denoising neural network configured to output a denoised magnetic resonance image data in response to receiving the intermediate magnetic resonance image data and the synthetic magnetic resonance image data as input. Execution of the machine-executable instructions further causes the processor to receive the filtered magnetic resonance image data by inputting the intermediate magnetic resonance image data and the synthetic magnetic resonance image data into the image denoising neural network. The denoised magnetic resonance image data is used as input into the iterative algorithm to generate the intermediate magnetic resonance image data repeatedly. In this embodiment the denoising neural network is configured as a filtering network. The filter is dependent upon the values of the synthetic magnetic resonance image data.

In another embodiment the imaging generating neural network is further configured to receive a configuration vector as input. The configuration vector specifies the first configuration of the magnetic resonance imaging system and the second configuration of the magnetic resonance imaging system. In this embodiment the input generating neural network is configured by the configuration vector to control its input and output format. The use of the configuration vectors may allow to train a single network that works for a variety of pairs of configurations but it may require a larger amount of training.

In another embodiment the medical system further comprises at least one magnetic resonance imaging system. For example, the first configuration could be for a first magnetic resonance imaging system and the second configuration could be for a second magnetic resonance imaging system. In other instances, there is only one magnetic resonance imaging system and both the measured k-space data and the reference magnetic resonance image data are acquired on the same magnetic resonance imaging system. Various functions of the magnetic resonance imaging system that are implemented in software such as the image generating neural network and the reconstruction may be remotely accessible or they may be installed in the computational system to control the magnetic resonance imaging system.

The memory further contains first pulse sequence commands configured to control the at least one magnetic resonance imaging system to acquire the measured k-space data. The memory further contains second pulse sequence commands configured to control the at least one magnetic resonance imaging system to acquire the reference k-space data. Execution of the machine-executable instructions further causes the computational system to acquire the reference k-space data by controlling the magnetic resonance imaging system with the second pulse sequence commands. Execution of the machine-executable instructions further causes the computational system to reconstruct the reference magnetic resonance image from the reference k-space data. Execution of the machine-executable instructions further causes the computational system to acquire the measured k-space data by controlling the magnetic resonance imaging system with the first pulse sequence commands.

In another embodiment execution of the machine-executable instructions further causes the computational system to construct synthetic k-space data using the synthetic magnetic resonance image. Execution of the machine-executable instructions further causes the computational system to control acquisition of the measured k-space data using the synthetic k-space data. For example, as the measured k-space data is acquired in groups or shots this acquired measured k-space data can be directly compared to the synthetic k-space data and this may be used to control or modify the acquisition of further measured k-space data.

In another embodiment execution of the machine-executable instructions causes the computational system to control the acquisition of the measured k-space data by choosing a k-space data sampling pattern for the first pulse sequence commands using the synthetic k-space data. The signal in k-space has an inhomogeneous power density. By examining the synthetic k-space data it can then be inferred which are the important portions of k-space to choose as a sampling pattern when sampling the measured k-space data. For example, the algorithm could look at the synthetic k-space data and see where the power density is the highest and then modify the k-space data sampling pattern to sample accordingly.

In another embodiment the first pulse sequence commands are configured to control the magnetic resonance imaging system to acquire the measured k-space data in groups of k-space data. Execution of the machine-executable instructions further causes the computational system to calculate a comparison metric between the synthetic k-space data and each of the groups of k-space data. Execution of the machine-executable instructions further causes the computational system to perform a predetermined action if the comparison metric is outside of a predetermined range value. For example, the comparison metric could calculate a similarity or perform a pattern matching operation between the synthetic k-space data and an acquired group of k-space data. If it matches below a predetermined amount then the predetermined action is triggered. In another embodiment the predetermined action is any one of the following: a re-acquisition of at least a portion of the groups of k-space data, a halting of the acquisition of the measured k-space data and combinations thereof.

In another embodiment the corrected magnetic resonance image is reconstructed according to a parallel imaging magnetic resonance imaging reconstruction algorithm. This for example may also be combined with compressed sensing.

In another aspect the invention provides for a method of operating a medical system. The method comprises receiving measured k-space data acquired according to a first configuration of a magnetic resonance imaging system. The measured k-space data is descriptive of a region of interest of a subject. The method further comprises receiving reference magnetic resonance image data. The reference magnetic resonance image data is descriptive of a region of interest of the subject. The reference magnetic resonance image data is acquired according to a second configuration of the magnetic resonance imaging system. The method further comprises receiving synthetic magnetic resonance image data by inputting the reference magnetic resonance image into an image generating neural network. The image generating neural network is configured for outputting the synthetic magnetic resonance image data in response to receiving the reference magnetic resonance image data as input.

The image generating neural network is configured to generate the synthetic magnetic resonance image data as a simulation of magnetic resonance image data acquired according to the first configuration of the magnetic resonance imaging system when the reference magnetic resonance image data is acquired according to the second configuration of the magnetic resonance imaging system. The method further comprises reconstructing corrected magnetic resonance image data from the measured k-space data and the synthetic magnetic resonance image data.

In another aspect the invention provides for a computer program that comprises machine-executable instructions for execution by a computational system controlling the medical system. The computer program further comprises an image generating neural network that is configured for outputting synthetic magnetic resonance image data in response to receiving reference magnetic resonance image data as input. The image generating neural network is configured to generate the synthetic magnetic resonance image data as a simulation of magnetic resonance image data acquired according to a first configuration of a magnetic resonance imaging system when the reference magnetic resonance image data is acquired according to a second configuration of the magnetic resonance imaging system.

Execution of the machine-executable instructions causes the computational system to receive measured k-space data acquired according to the first configuration of the magnetic resonance imaging system. The measured k-space data is descriptive of a region of interest of a subject. The reference magnetic resonance image data is acquired according to the second configuration of the magnetic resonance imaging system. The reference magnetic resonance imaging system is descriptive of the region of interest of the subject. Execution of the machine-executable instructions further causes the computational system to receive the synthetic magnetic resonance image data by inputting the reference magnetic resonance image into the image generating neural network. Execution of the machine-executable instructions further causes the computational system to reconstruct the corrected magnetic resonance image data from the measured k-space data and the synthetic magnetic resonance image data.

In another aspect the invention provides for a magnetic resonance imaging system. The magnetic resonance imaging system comprises a memory storing machine-executable instructions and an image generating neural network. The image generating neural network is configured for outputting synthetic magnetic resonance image data in response to receiving a reference magnetic resonance image data as input. The image generating neural network is configured to generate the synthetic magnetic resonance image as a simulation of a magnetic resonance image acquired according to a first configuration of the magnetic resonance imaging system when the reference magnetic resonance image data is acquired according to a second configuration of the magnetic resonance imaging system.

The memory further contains the first pulse sequence commands configured to control the magnetic resonance imaging system to acquire the measured k-space data. The memory further contains the second pulse sequence commands configured to control the magnetic resonance imaging system to acquire the reference k-space data. The magnetic resonance imaging system further comprises a computational system configured for controlling the medical system.

Execution of the machine-executable instructions causes the computational system to acquire the reference k-space data by controlling the magnetic resonance imaging system with the second pulse sequence commands. Execution of the machine-executable instructions further causes the computational system to reconstruct the reference magnetic resonance image data from the reference k-space data. Execution of the machine-executable instructions further causes the computational system to construct synthetic k-space data using the synthetic magnetic resonance image data. Execution of the machine-executable instructions further causes the computational system to control acquisition of the measured k-space data using the first pulse sequence commands and the synthetic k-space data. For example, the synthetic k-space data can be compared to groups or shots of the measured k-space data as it is measured and used to adapt the acquisition of further measured k-space data in real time.

In another embodiment, execution of the machine-executable instructions causes the computational system to control the acquisition of the measured k-space data by choosing a k-space data sampling pattern for the first pulse sequence commands using the synthetic k-space data. For example, the synthetic k-space data can be used to choose the k-space data sampling pattern and used to modify the first pulse sequence commands before they are executed. In this embodiment, one first calculates the synthetic k-space data. have the synthetic k-space data and use this k-space data to adjust the sampling pattern. The k-space is sparse, so you use the synthetic k-space data to predict where one should sample more.

The first pulse sequence commands are configured to control the magnetic resonance imaging system to acquire the measured k-space data in groups of k-space data. Execution of the machine-executable instructions further causes the computational system to calculate a comparison metric between the synthetic k-space data and each of the groups of k-space data. Execution of the machine-executable instructions further causes the computational system to perform a predetermined action if the comparison metric is outside of a predetermined value range.

In another embodiment the predetermined action is any one of the following: a re-acquisition of at least a portion of the groups of k-space data, a halting of the acquisition of the measured k-space data, and combinations thereof.

Various embodiments may possibly be described by one or more of the following numbered clauses:

Clause 1. A feature comprising a medical system, wherein the medical system comprises:

a memory storing machine executable instructions and an image generating neural network, wherein the image generating neural network is configured for outputting synthetic magnetic resonance image data in response to receiving reference magnetic resonance image data as input, wherein the image generating neural network is configured to generate the synthetic magnetic resonance image data as a simulation of magnetic resonance image data acquired according to a first configuration of a magnetic resonance imaging system when the reference magnetic resonance image data is acquired according to a second configuration of the magnetic resonance imaging system;

a computational system configured for controlling the medical system, wherein execution of the machine executable instructions causes the computational system to:

receive measured k-space data acquired according to the first configuration of the magnetic resonance imaging system, wherein the measured k-space data is descriptive of a region of interest of a subject;

receive the reference magnetic resonance image data, wherein the reference magnetic resonance image data is descriptive of the region of interest of the subject;

receive the synthetic magnetic resonance image data by inputting the reference magnetic resonance image data into the image generating neural network; and reconstruct corrected magnetic resonance image data from the measured k-space data and the synthetic magnetic resonance image data.

Clause 2. The medical system of clause 1, wherein the image generating neural network is configured for receiving the reference magnetic resonance image data according to a predetermined input format, wherein execution of the machine executable instructions further causes the computational system to:

convert the reference magnetic resonance image data to the predetermined input format before inputting the reference magnetic resonance image data into the image generating neural network; and spatially match the synthetic magnetic resonance image data to the measured k-space data before reconstructing the corrected magnetic resonance image data.

Clause 3. The medical system of clause 1 or 2, wherein the measured k-space data and the synthetic magnetic resonance image data are spatially matched.

Clause 4. The medical system of clause 1, 2, or 3, wherein the synthetic magnetic resonance image data provides prior knowledge during the reconstruction of the corrected magnetic resonance image data.

Clause 5. The medical system of the preceding clauses, wherein execution of the machine executable instructions further causes the computational system to reconstruct synthetic k-space data from the synthetic magnetic resonance image data, wherein the measured k-space data is divided into groups of k-space data, wherein the corrected magnetic resonance image data is reconstructed by using the synthetic k-space data to modify at least a portion of the groups of k-space data.

Clause 6. The medical system of clause 5, wherein execution of the machine executable instructions further causes the computational system to:

use the synthetic k-space data to determine a rigid body transformation or higher order transformation of one or more of the groups of k-space data; and perform a phase and amplitude correction of the one or more of the groups of k-space data using the rigid body transformation or higher order transformation.

Clause 7. The medical system of clause 5 or 6, wherein execution of the machine executable instructions further causes the computational system to:

use the synthetic k-space data to determine a configuration for a pre-defined motion model; and perform a correction of the one or more of the groups of k-space data using the pre-defined motion model.

Clause 8. The medical system of clause 7, wherein the pre-defined motion model is configured to provide a transformation of the synthetic k-space data equivalent to an affine or elastic transformation in image space.

Clause 9. The medical system of any one of clauses 5 through 8, wherein execution of the machine executable instructions further causes the computational system to:

detect at least one incomplete k-space sampling region in the measured k-space data; and fill the incomplete k-space sampling region in the measured k-space data with the synthetic k-space data.

Clause 10. The medical system of any one of clause 5 through 9, wherein execution of the machine executable instructions further causes the computational system to:

receive a motion signal descriptive of motion of the subject;

reconstruct the corrected magnetic resonance image data using the groups of k-space data which have a motion signal within a predetermined range.

Clause 11. The medical system of clause 10, wherein execution of the machine executable instructions further causes the computation system to:

calculate the motion signal as a synthetic motion signal by comparing the synthetic k-space data to each of the groups of k-space data;

Clause 12. The medical system of any one of clause 5 through 11, wherein the memory further contains an image quality evaluation module configured for outputting an image quality metric, wherein execution of the machine executable instructions further causes the computational system to:

generate multiple k-space data sets by systematically replacing combinations of the groups of k-space data with portions of the synthetic k-space data;

generate multiple trial magnetic resonance image data by reconstructing each of the multiple k-space data sets; and select the corrected magnetic resonance image data from the multiple trial magnetic resonance image data by optimizing the image quality metric output by the image quality evaluation module.

Clause 13. The medical system of clause 12, wherein image quality metric is determined using any one of the following:

a registration between the synthetic magnetic resonance image data and one of the multiple trial magnetic resonance image data;

an output from a trained neural network that outputs the image quality metric in response to inputting one of the multiple trial magnetic resonance image data;

by calculating a total image gradient; and by calculating an image entropy.

Clause 14. The medical system of any one of clauses 5 through 13, wherein execution of the machine executable instructions further causes the computational system to:

reconstruct multiple corrected magnetic resonance image data; and perform any one of the following: provide the corrected magnetic resonance image data as an average of the multiple corrected magnetic resonance image data and provide the corrected magnetic resonance image data as a selection of the multiple corrected magnetic resonance image data.

Clause 15. The medical system of any one of clauses 5 through 14, wherein the reconstruction of the corrected magnetic resonance image data from the measured k-space data and the synthetic magnetic resonance image data is formulated as an optimization problem that assigns weighting factors to each of the groups of k-space data, wherein execution of the machine executable instructions further causes the computational system to:

identify at least one corrupted group of k-space data selected from the groups of k-space data; and correct the at least one corrupted group of k-space data using the synthetic k-space data;

assign the weighting factors to each of the groups of k-space data, wherein the at least one corrupted group of k-space data is assigned a reduced value weighting factor.

Clause 16. The medical system of clause 15, wherein the at least one corrupted group of k-space data selected from the groups of k-space data is detected by any one of the following: using an external navigator signal, detecting missing k-space data, by a comparison with the synthetic k-space data, and combinations thereof.

Clause 17. The medical system of clause 15 or 16, wherein the correction of the at least one corrupted group of k-space data using the synthetic k-space data is performed using any one of the following: replacing the at least one corrupted group of k-space data with the synthetic k-space data, modifying or shifting the at least one corrupted group of k-space data, appending the synthetic k-space data to the at least one corrupted group of k-space data, and combinations thereof.

Clause 18. The medical system of any one of the preceding clauses, wherein the corrected magnetic resonance image data is reconstructed according to a compressed sensing image reconstruction algorithm.

Clause 19. The medical system of clause 18, wherein the compressed sensing image reconstruction algorithm is an iterative algorithm that generates an intermediate magnetic resonance image repeatedly, wherein the compressed sensing image reconstruction algorithm comprises denoising the intermediate magnetic resonance image using the synthetic magnetic resonance image data.

Clause 20. The medical system of clause 19, wherein the compressed sensing image reconstruction algorithm is configured to generate the intermediate magnetic resonance image data by solving an optimization problem, wherein the optimization problem includes a regularization term, wherein the regularization term is a function of the synthetic magnetic resonance image data and performs the denoising of the intermediate magnetic resonance image data using the synthetic magnetic resonance image data.

Clause 21. The medical system of clause 19, wherein the memory further contains an image denoising neural network configured to output denoised magnetic resonance image data in response to receiving the intermediate magnetic resonance image data and the synthetic magnetic resonance image data as input, wherein execution of the machine executable instructions further causes the processor to receive the filtered magnetic resonance image data by inputting the intermediate magnetic resonance image data and the synthetic magnetic resonance image data into the image denoising neural network, wherein the denoised magnetic resonance image data is used as input into the iterative algorithm to generate the intermediate magnetic resonance image data repeatedly.

Clause 22. The medical system of any one of the preceding clauses, wherein the image generating neural network is further configured to receive a configuration vector as input, wherein the configuration vector specifies the first configuration of the magnetic resonance imaging system and the second configuration of the magnetic resonance imaging system.

Clause 23. The medical system of any one of the preceding clauses, wherein the medical system further comprise at least one magnetic resonance imaging system, wherein the memory further contains first pulse sequence commands configured to control the at least one magnetic resonance imaging system to acquire the measured k-space data, wherein the memory further contains second pulse sequence commands configured to control the at least one magnetic resonance imaging system to acquire the reference k-space data, wherein execution of the machine executable instructions further causes the computational system to:

acquire the reference k-space data by controlling the magnetic resonance imaging system with the second pulse sequence commands;

reconstruct the reference magnetic resonance image data from the reference k-space data; and acquire the measured k-space data by controlling the magnetic resonance imaging system with the first pulse sequence command.

Clause 24. The medical system of clause 23, wherein execution of the machine executable instructions further causes the computational system to:

construct synthetic k-space data using the synthetic magnetic resonance image data; and control acquisition of the measured k-spaced data using the synthetic k-space data.

Clause 25. The medical system of clause 24, wherein execution of the machine executable instructions causes the computational system to control the acquisition of the measured k-space data by choosing a k-space sampling pattern for the first pulse sequence commands using the synthetic k-space data.

Clause 26. The medical system of clause 24 or 25, wherein the first pulse sequence commands are configured to control the magnetic resonance imaging system to acquire the measured k-space data in groups of k-space data, wherein execution of the machine executable instructions further causes the computational system to:

calculate a comparison metric between the synthetic k-space data and each of the groups of k-space data; and perform a predetermined action if the comparison metric is outside of a predetermined value range.

Clause 27. The medical system of clause 26, wherein the predetermined action is any one of the following: a reacquisition of at least a portion of the groups of k-space data, a halting of the acquisition of the measured k-space data, and combinations thereof.

Clause 28. The medical system of any one of the preceding clauses, wherein the corrected magnetic resonance image data is reconstructed according to a parallel imaging magnetic resonance imaging reconstruction algorithm.

Clause 29. A feature of a method of operating a medical system, wherein the method comprises:

receiving measured k-space data acquired according to a first configuration of a magnetic resonance imaging system, wherein the measured k-space data is descriptive of a region of interest of a subject;

receiving reference magnetic resonance image data acquired according to a second configuration of the magnetic resonance imaging system, wherein the reference magnetic resonance image data is descriptive of the region of interest of the subject;

receiving synthetic magnetic resonance image data by inputting the reference magnetic resonance image data into an image generating neural network, wherein the image generating neural network is configured for outputting the synthetic magnetic resonance image data in response to receiving the reference magnetic resonance image data as input, wherein the image generating neural network is configured to generate the synthetic magnetic resonance image data as a simulation of magnetic resonance image data acquired according to the first configuration of the magnetic resonance imaging system when the reference magnetic resonance image data is acquired according to the second configuration of the magnetic resonance imaging system; and reconstructing corrected magnetic resonance image data from the measured k-space data and the synthetic magnetic resonance image data.

Clause 30. A feature of a computer program comprising machine executable instructions for execution by a computational system controlling a medical system, wherein the computer program further comprises an image generating neural network configured for outputting synthetic magnetic resonance image data in response to receiving reference magnetic resonance image data as input, wherein the image generating neural network is configured to generate the synthetic magnetic resonance image data as a simulation of magnetic resonance image data acquired according to a first configuration of a magnetic resonance imaging system when the reference magnetic resonance image data is acquired according to a second configuration of the magnetic resonance imaging system, wherein execution of the machine executable instructions causes the computational system to:

receive measured k-space data acquired according to the first configuration of the magnetic resonance imaging system, wherein the measured k-space data is descriptive of a region of interest of a subject;

receive the reference magnetic resonance image data, wherein the reference magnetic resonance image data is descriptive of the region of interest of the subject;

receive the synthetic magnetic resonance image data by inputting the reference magnetic resonance image data into the image generating neural network; and reconstruct corrected magnetic resonance image data from the measured k-space data and the synthetic magnetic resonance image data.

Clause 31. A feature of a magnetic resonance imaging system, wherein the magnetic resonance imaging system comprises:

a memory storing machine executable instructions and an image generating neural network, wherein the image generating neural network is configured for outputting synthetic magnetic resonance image data in response to receiving a reference magnetic resonance image data as input, wherein the image generating neural network is configured to generate the synthetic magnetic resonance image data as a simulation of a magnetic resonance image data acquired according to a first configuration of a magnetic resonance imaging system when the reference magnetic resonance image data is acquired according to a second configuration of the magnetic resonance imaging system, wherein the memory further contains first pulse sequence commands configured to control the magnetic resonance imaging system to acquire the measured k-space data, wherein the memory further contains second pulse sequence commands configured to control the magnetic resonance imaging system to acquire reference k-space data;

a computational system configured for controlling the medical system, wherein execution of the machine executable instructions causes the computational system to:

acquire the reference k-space data by controlling the magnetic resonance imaging system with the second pulse sequence commands;

reconstruct the reference magnetic resonance image data from the reference k-space data;

receive the synthetic magnetic resonance image data by inputting the reference magnetic resonance image data into the image generating neural network construct synthetic k-space data using the synthetic magnetic resonance image data; and control acquisition of the measured k-spaced data using the first pulse sequence commands and the synthetic k-space data.

Clause 32. The magnetic resonance imaging system of clause 31, wherein execution of the machine executable instructions causes the computational system to control the acquisition of the measured k-space data by choosing a k-space sampling pattern for the first pulse sequence commands using the synthetic k-space data.

Clause 33. The magnetic resonance imaging system of clause 31 or 32, wherein the first pulse sequence commands are configured to control the magnetic resonance imaging system to acquire the measured k-space data in groups of k-space data, wherein execution of the machine executable instructions further causes the computational system to:

calculate a comparison metric between the synthetic k-space data and each of the groups of k-space data; and perform a predetermined action if the comparison metric is outside of a predetermined value range.

Clause 34. The magnetic resonance imaging system of clause 33, wherein the predetermined action is any one of the following: a reacquisition of at least a portion of the groups of k-space data, a halting of the acquisition of the measured k-space data, and combinations thereof.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan. Magnetic resonance data is an example of tomographic medical image data.

A Magnetic Resonance Imaging (MRI) image, MR image, or magnetic resonance imaging data is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
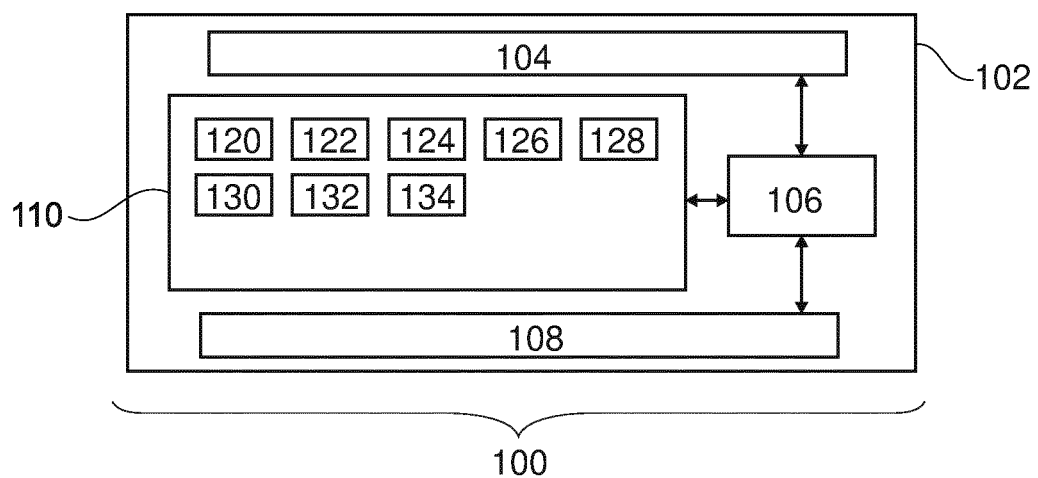
FIG. 1 illustrates an example of a medical system.

FIG. 1 illustrates an example of a medical system 100. The medical system in FIG. 1 is shown as comprising a computer which has a computational system 106. The computational system 106 is intended to represent one or more computational systems such as processors or cores located at one or more locations. The computational system 106 is shown as being connected to an optional hardware interface 104. If other components of the medical system 100 such as a magnetic resonance imaging system are present, then the hardware interface 104 could be used by the computational system 106 to communicate with it and control it. The medical system 100 is further shown as comprising an optional user interface 108 that may enable an operator to use and control the medical system 100. The medical system 100 is further shown as containing a memory 110 that is also connected to the computational system 106. The memory 110 is intended to represent any memory or storage that is connected to the computational system 106.

The memory 110 is shown as containing machine-executable instructions 120. The machine-executable instructions 120 enable the processor 106 to perform various image processing, data processing and control functions. The memory 110 is further shown as containing an image generating neural network. The image generating neural network 122 is configured to receive a reference magnetic resonance image and then output a synthetic magnetic resonance image data 128. The reference magnetic resonance image data 126 is acquired or configured according to a second configuration of the magnetic resonance imaging system and the synthetic magnetic resonance image data 128 is a simulation of magnetic resonance image data acquired according to a first configuration of a magnetic resonance imaging system.

The image generating neural network 122 may therefore enable previously acquired data to be used to either control or improve the generation of a corrected magnetic resonance image data. The memory 110 is further shown as containing examples of the reference magnetic resonance image data 126 and the output synthetic magnetic resonance image data 128. Once the synthetic magnetic resonance image data 128 has been obtained it may optionally be used to calculate synthetic k-space data 130. For example, a knowledge of the first configuration of the magnetic resonance imaging system may enable the calculation of the synthetic k-space data 130 that is sampled in the same way that the measured k-space data 124 would be. The measured k-space data 124 acquired by a magnetic resonance imaging system acquired using the first configuration is also shown as being stored in the memory 110.

The memory 110 is further shown as containing a corrected magnetic resonance image data 132. This for example may be calculated using the measured k-space data 124 and either the synthetic k-space data 130 or the synthetic magnetic resonance image data 128. The synthetic k-space data 130 may be used to correct or replace portions of the measured k-space data 124. In other instances, the synthetic magnetic resonance image data 128 may be used as prior knowledge to improve the reconstruction of the corrected magnetic resonance image data 132 from the measured k-space data 124.

The memory 110 is also shown as containing an optional image processing module 134. This module may for example be used for conditioning the reference magnetic resonance image data 126 such that it has a predetermined image format before it is input into the image generating neural network 122. Likewise, the image processing module 134 may also be used to configure or modify the synthetic magnetic resonance image data 128 such that it is spatially matched to the measured k-space data 124.

Figure 2:
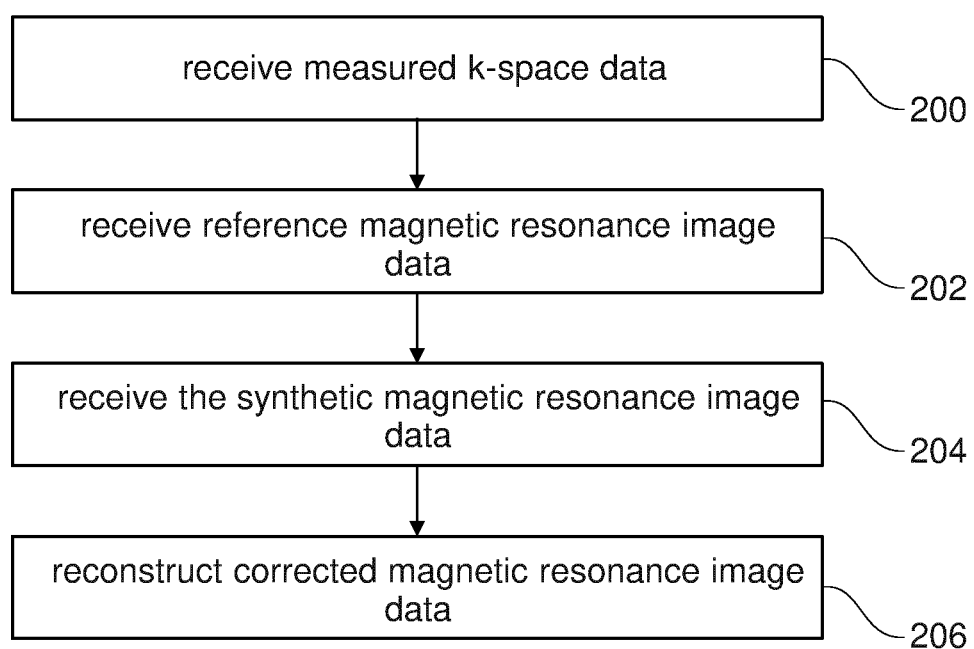
FIG. 2 shows a flow chart which illustrates a method of operating the medical system of FIG. 1.

FIG. 2 shows a flowchart which illustrates a method of operating the medical system 100 of FIG. 1. First, in step 200, the measured k-space data 124 is received. Next, in step 202, the reference magnetic resonance image data 126 is also received. Next, in step 204, the synthetic magnetic resonance image data 128 is received by inputting the reference magnetic resonance image data 126 into the image generating neural network 122. It should be noted that step 200 may also be performed after step 202 or 204. The synthetic magnetic resonance image data 128 or the synthetic k-space data 130 is then used in step 206. In step 206, the corrected magnetic resonance image data 132 is reconstructed using the measured k-space data 124 and the synthetic magnetic resonance image data 128 or alternatively the synthetic k-space data 130.

Figure 3:
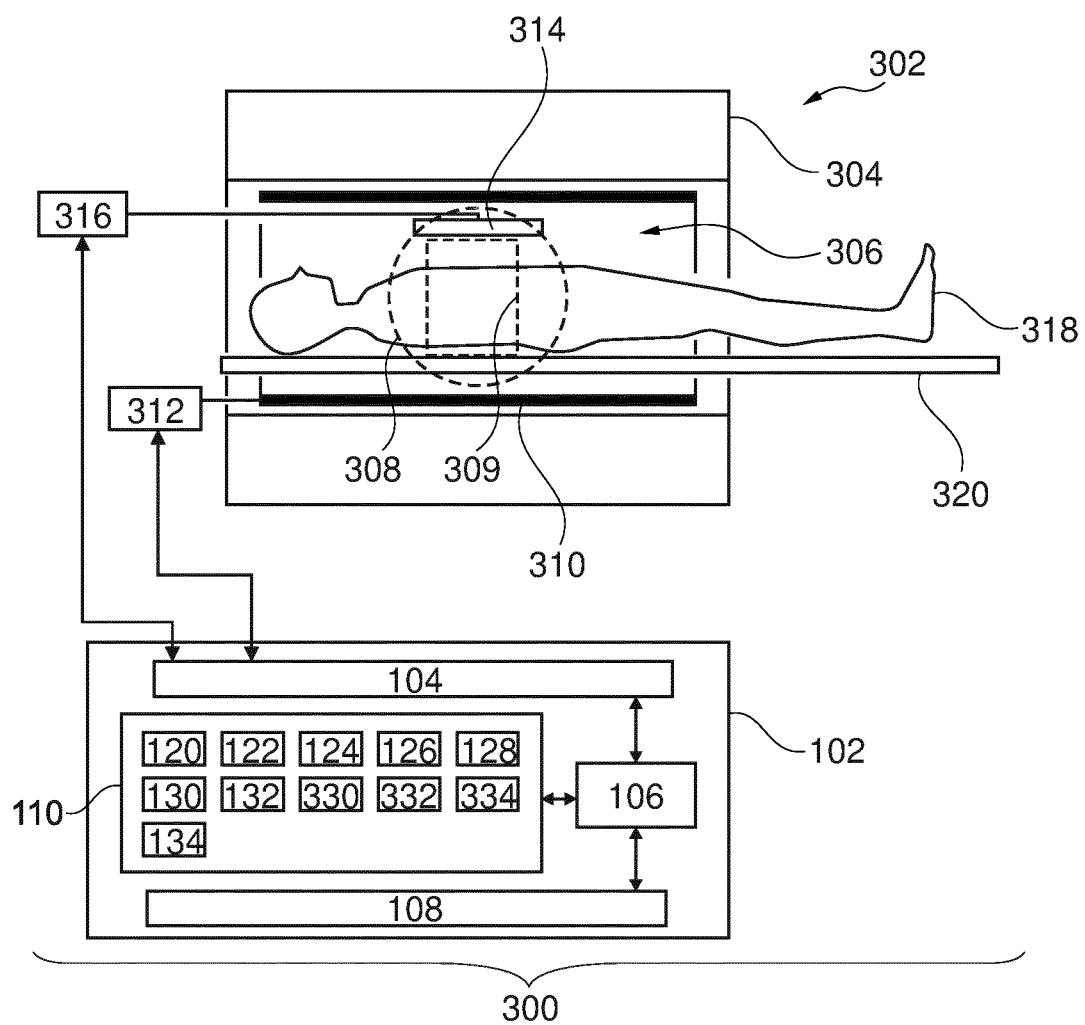
FIG. 3 illustrates a further example of a medical system.

FIG. 3 illustrates a further example of the medical system 300. The medical system illustrated in FIG. 3 is similar to the medical system 100 of FIG. 1 except that it additionally comprises a magnetic resonance imaging system 302.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. A region of interest 309 is shown within the imaging zone 308. The magnetic resonance data that is acquired typically acquired for the region of interest. A subject 318 is shown as being supported by a subject support 320 such that at least a portion of the subject 318 is within the imaging zone 308 and the region of interest 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The transceiver 316 and the gradient controller 312 are shown as being connected to the hardware interface 106 of a computer system 102.

The memory 110 is further shown as containing first pulse sequence commands 330 that are configured for acquiring the measured k-space data 124 while the magnetic resonance imaging system 302 is in a first configuration. The second pulse sequence commands 332 are configured for acquiring reference k-space data 334 when the magnetic resonance imaging system 302 is in a second configuration. The memory 110 is further shown as containing the reference k-space data 334 that has been acquired when the second pulse sequence commands 332 are executed. The measured k-space data 124 may be acquired when the first pulse sequence commands 330 are acquired.

In some instances, the reference k-space data 334 and the measured k-space data 124 could be acquired at different times for the same subject 318 or even in different magnetic resonance imaging systems 302. In this example both are acquired during the same examination. They could for example both be acquired for the same region of interest 309 and be acquired in a spatially matched fashion.

Figure 4:
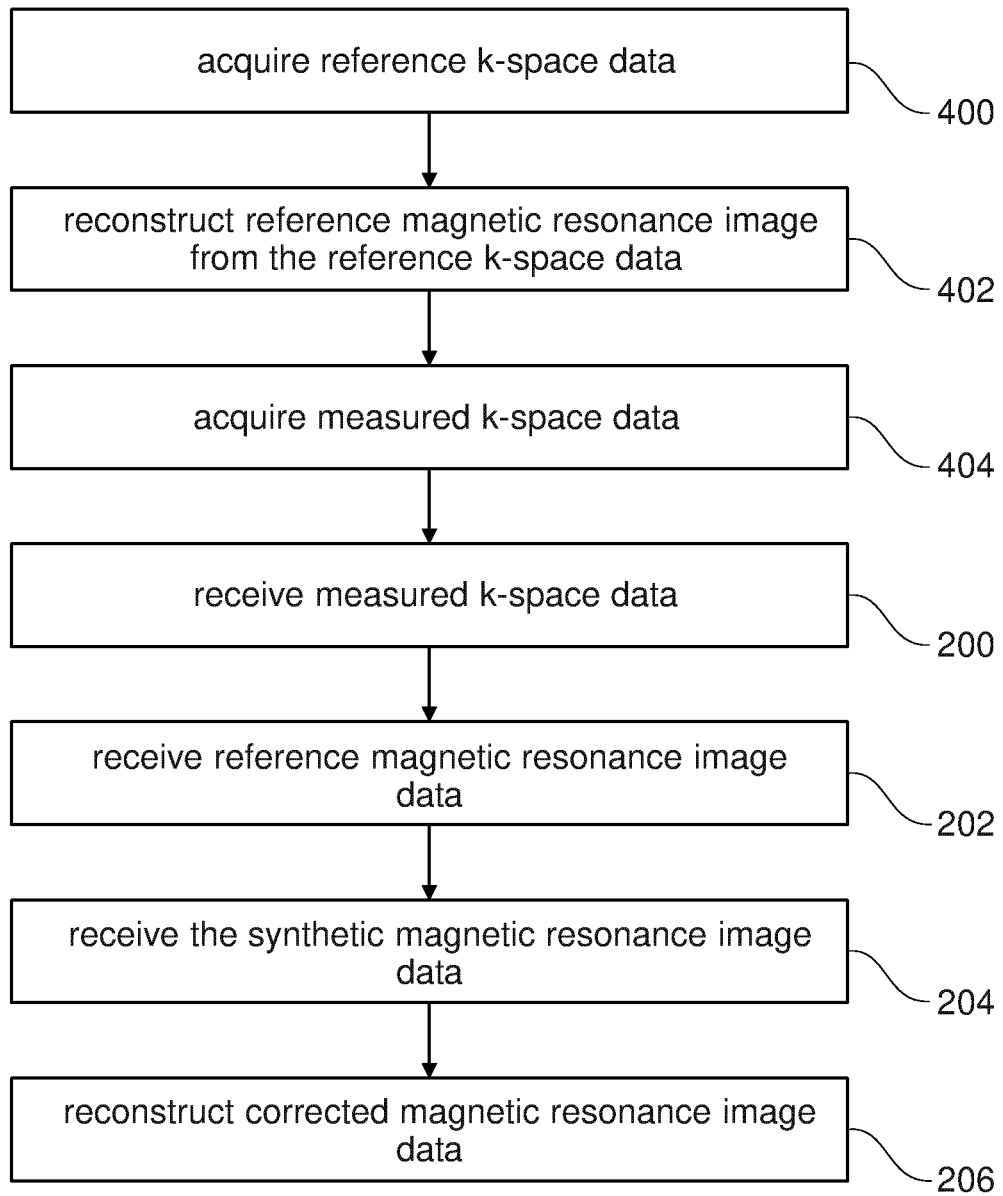
FIG. 4 shows a flow chart which illustrates a method of operating the medical system of FIG. 3.

FIG. 4 shows a flowchart which illustrates a method of operating the medical system 300 of FIG. 3. First in step 400 the reference k-space data 334 is acquired by controlling the magnetic resonance imaging system with the second pulse sequence commands 332. Next, in step 402, the reference magnetic resonance image data 126 is reconstructed from the reference k-space data 334. Next, in step 404, the measured k-space data 124 is acquired by controlling the magnetic resonance imaging system 302 with the first pulse sequence commands 330. After step 404 the method proceeds and performs steps 200, 202, 204, and 206 as was illustrated in FIG. 2.

Figure 5:
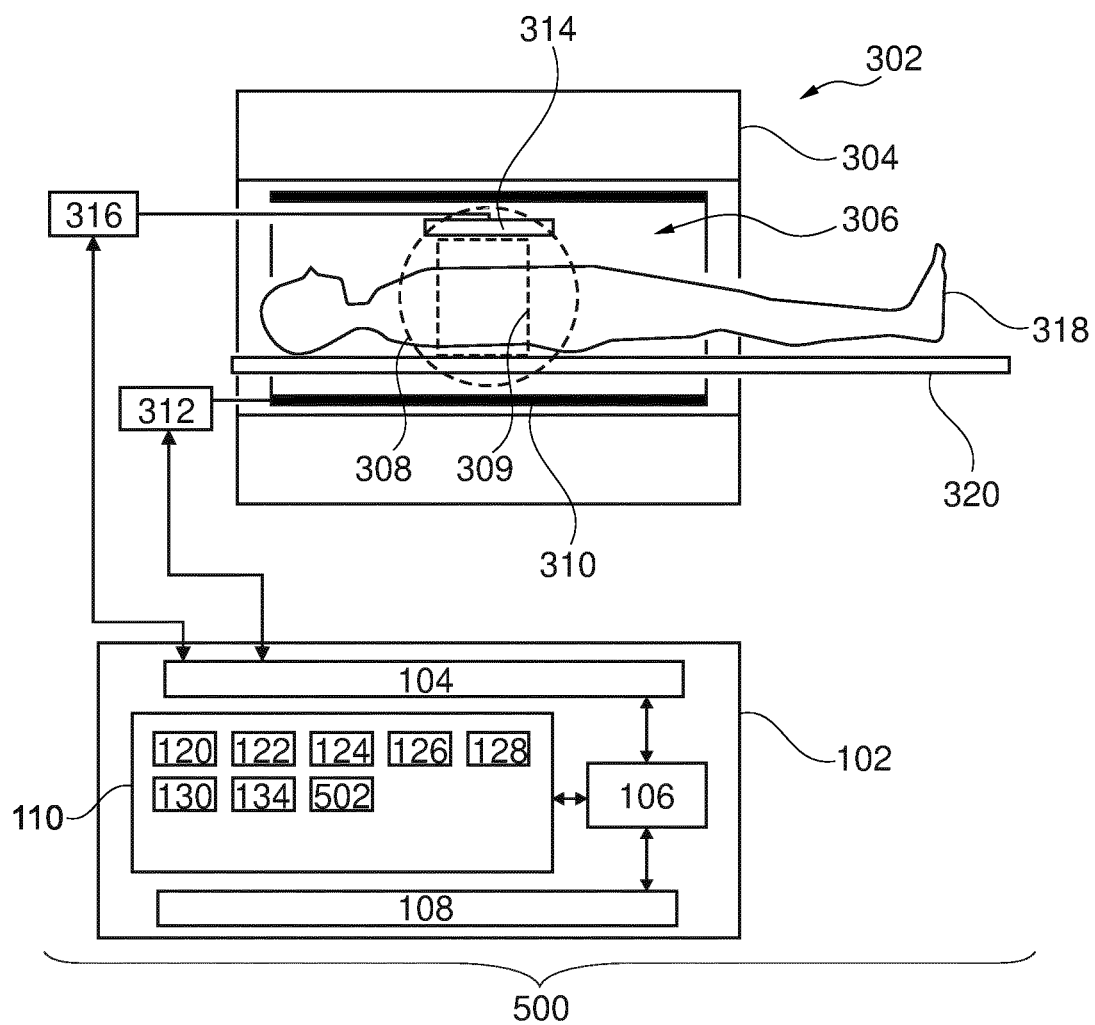
FIG. 5 illustrates a further example of a medical system.

FIG. 5 illustrates an example of a magnetic resonance imaging system 500. The magnetic resonance imaging system 500 is similar to the medical system 300 of FIG. 3 except that the contents of the memory 110 are different. In this example the machine-executable instructions 120 are configured such that the synthetic k-space data 130 is used to modify the acquisition of the measured k-space data 124. This for example may be useful for correcting for motion of the subject 318 as well as the failure of various channels of the radio-frequency system or noise received by the RF antenna 314.

The memory 110 is shown as containing a corrected magnetic resonance image 502 that was constructed from the measured k-space data 124. The synthetic k-space data 130 may be used in several different ways to correct for the measured k-space data 124. For example, the synthetic k-space data 130 could be used to choose a sampling pattern for the first pulse sequence commands 330 which would effectively choose the sample locations of the measured k-space data 124. In other examples, the synthetic k-space data 130 could be compared to shots or groups of measured k-space data 124 as they are acquired and used to correct the acquisition or to adjust the measured k-space data 124. This could be done on the fly or after all of the measured k-space data 124 has been acquired. The features of FIG. 5 may be combined with the features of FIGS. 1 and 3.

Figure 6:
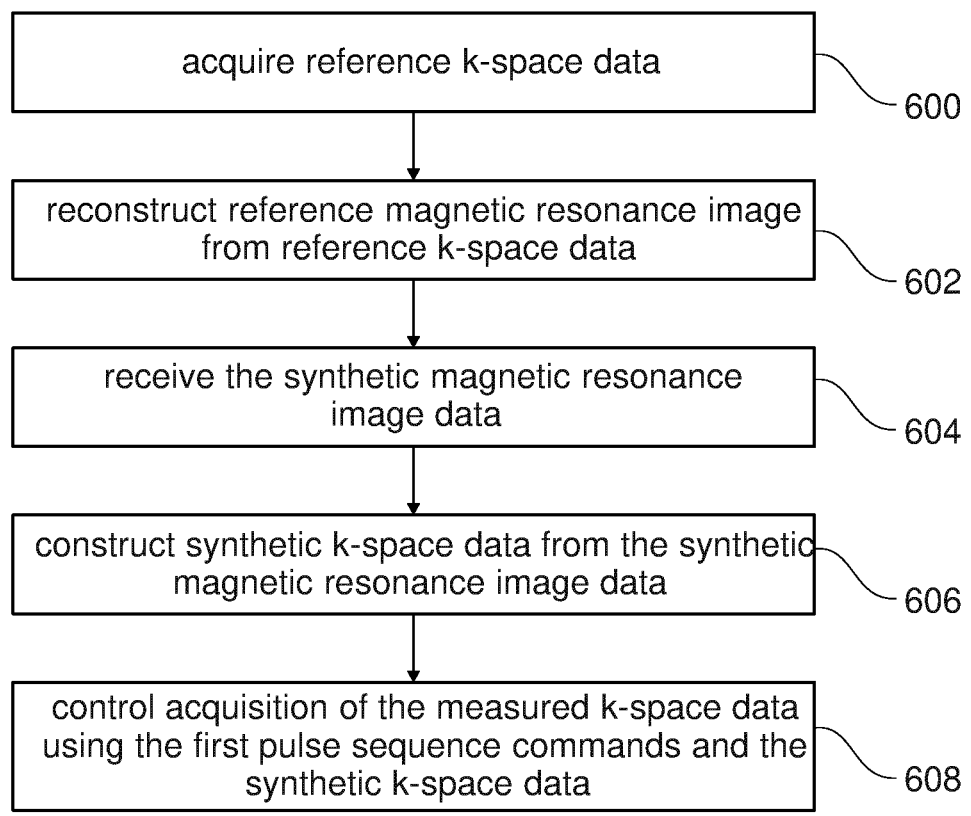
FIG. 6 shows a flow chart which illustrates a method of operating the medical system of FIG. 5.

FIG. 6 shows a flowchart which illustrates a method of operating the magnetic resonance imaging system 500 of FIG. 5. First in step 600 the reference k-space data 334 is acquired by controlling the magnetic resonance imaging system 500 with the second pulse sequence commands 332. Next, in step 602, the reference magnetic resonance image data 126 is reconstructed from the reference k-space data 334. Next, in step 604, the synthetic magnetic resonance image data 128 is received by inputting the reference magnetic resonance image data 126 into the image generating neural network 122. Next, in step 606, the synthetic k-space data 130 is constructed from the synthetic magnetic resonance image data 128. This for example may be constructed using an inverse Fourier transform. Finally, in step 608, the magnetic resonance imaging system is controlled with the first pulse sequence commands 330 in order to acquire the measured k-space data 124. In step 608, the acquisition is also controlled or adjusted using the synthetic k-space data 130.

The speed limitations inherent to MRI acquisitions have triggered research on numerous image reconstruction techniques that allow obtaining good image quality from under-sampled k-space data. The most prominent of these techniques are parallel imaging (PI), compressed sensing (CS) and their combination, PI-CS. Recently, the use of neural networks and deep learning (DL) has shown to enable PI-CS to reach even higher acceleration rates while preserving image quality. This is possible because neural networks can better capture the low-dimensional space of MRI images, which they learn during training from large datasets containing images from many other patients.

Some examples disclosed herein use the fact that in MM exams, multiple scans of the same anatomy are usually acquired with different contrasts (configurations of the magnetic resonance imaging system). As used herein a "contrast" is a configuration of a magnetic resonance imaging system used to acquire k-space data.

These different contrasts contain common information (same patient, same pathology, etc.), which can be taken advantage of in a compressed sensing reconstruction, if a good model of how the different contrasts are correlated is available. Such a CS reconstruction is called multi-contrast CS. Previous multi-contrast CS approaches have used simple analytical models to describe the correlation between contrasts. Here, we propose to use a neural network to learn this correlation from real data, allowing to reach higher acceleration factors maintaining high image quality.

The above-mentioned acceleration methods rely on the use of prior information. For parallel imaging coil sensitivities can be seen as a kind of prior information while for compressed sensing, image sparsity is a prior: either generic for all types of images (in the case of CS with wavelets for example), or generic for MM images (DL-CS, where a representation can be learnt, facilitated e.g. by a network trained on large quantities of MRI data). The improved performance of DL-CS compared to CS comes from the fact that the prior information used is better adapted because more specific to the type of images to be reconstructed. A logical further step leading to even better prior knowledge would be to include patient-specific information. This is the approach taken in multi-contrast CS (MC-CS), in which several images of the same anatomy acquired with different contrasts are either reconstructed simultaneously, or sequentially but taking into account the previous reconstructions. This is motivated by the fact that these different contrasts visibly contain correlated information (see FIGS. 7 and 10 below).

The main problem in MC-CS is the difficulty to model the shared information between contrasts. In the following, a Bayesian estimation setting is used to motivate the mathematical formulation of the problem. However, other approaches can be taken as well to justify the mathematical formulation of the MC-CS problem.

Calling x the image to be reconstructed, by the under-sampled measurements and A the (undersampled, multi-coil) measurement operator, Bayesian CS aims at providing an estimate of x as the minimal-mean-squared-error (MMSE) or maximum a posteriori (MAP) of the posterior distribution:

$$p_{x|y}(x|y) \propto p_x(x) p_{y|x}(y|x)$$

where $p_x(x)$ is the prior, $\propto$ indicates proportionality up to a constant, and in the case of additive white Gaussian noise of variance $\lambda$ on the measurements, the posterior distribution $p_{y|x}(y|x)$ can be given being proportional to the following Gaussian distribution estimator of the residuals |y−Ax| (data minus the undersampling operator applied to the guessed image) normalized to noise $\lambda$:

$$p_{y|x}(y|x) \propto e^{-\frac{\|y-Ax\|_2^2}{2\lambda}}.$$

For actual MR images, the true prior distribution is not known, but assuming a Laplace distribution on the wavelet transform $\Psi x$ of x leads to good results that are sparse in wavelet space: $p_x(x) \propto e^{\|\Psi x\|_1}$. Taking the MAP (maximum a posteriori) of the (logarithm) of $p_{x|y}(x|y)(x|y)$ then leads to the common LASSO formulation of compressed sensing:

$$\hat{x} = \operatorname{argmin}_x \frac{1}{2}\|y - Ax\|_2^2 + \lambda \|\Psi x\|_1$$

A corresponding formulation can be made for multi-contrast compressed sensing. Here, we consider a setting with two images of different contrasts, x and x'. We suppose that a good reconstruction of x' is already available, and we want to use it to reconstruct x from the undersampled measurements y. Taking into account x' leads to the posterior distribution:

$$p_{x|(y,x')}(x|(y,x')) \propto p_x(x) p_{x|x'}(x|x') p_{y|x}(y|x),$$

and to the corresponding minimization problem:

$$\hat{x} = \operatorname*{argmin}_x \frac{1}{2}\|y - Ax\|_2^2 - \lambda \log(p_x(x)) - \lambda \log(p_{x|x'}(x \mid x')).$$

A difficulty is that $p_x(x)$ and $p_{x|x'}(x|x')$ are not known. However, this Bayesian derivation encourages to tackle the MC-CS problem by solving a minimization problem of the general form:

$$\hat{x} = \operatorname*{argmin}_x \frac{1}{2}\|y - Ax\|_2^2 - \lambda f(x) - \mu g(x, x'). \quad (1)$$

Note that this formulation can be straightforwardly extended to more than 2 contrasts and to joint reconstruction of 2 or more contrasts. In general, if x and x' are not perfectly registered to each other as a result of patient motion between the scans or mismatch of the scans' resolution, field of view and planning.

As a first approximation it is assumed that the images are perfectly registered to each other. Then, one possible assumption to make is that x and x' are sparse in the same basis T and that their supports in that basis have a high overlap. This motivates forms such as $p_{x|x'}(x|x') \propto e^{-\|(Tx, Tx')\|_1}$ and uses algorithms to solve the problem of finding x. However, just as analytical priors $p_x$ have only a limited capacity to fully capture the real underlying prior distribution, analytical assumptions for $p_{x|x'}$ also have limited predictive power.

Examples may for example encode the distribution $p_{x|x'}$ or the product $p_x(x) p_{x|x'}(x|x')$ in a neural network, and to use it as a building block in an iterative CS reconstruction that solves different minimization problems inspired from Eq. (1). In particular, one may for example:

(1) Train a contrast-to-contrast network N (image generating neural network 122) can be trained that takes as input an image from a well-defined contrast A (reference magnetic resonance image data 126) and outputs an estimate of the corresponding image (synthetic magnetic resonance image data 128) with well-defined contrast B (the first configuration of the magnetic resonance imaging system). This network can be trained using a training dataset of pairs of the same image with contrast A and B, and a loss function such as the MSE. Alternatively, one could use unpaired datasets of images with contrast A and other images with contrast B from different patients, using a conditional cycle-GAN. During the multi-contrast reconstruction, the network is then applied once on the image x' to produce an estimate $\bar{x} = N(x') \approx x$. This estimate $\bar{x}$ is then used in an iterative CS reconstruction producing:

$$\hat{x} = \operatorname*{argmin}_x \frac{1}{2}\|y - Ax\|_2^2 + \lambda \|\Psi x\|_1 + \mu \|T(x - \bar{x})\|_p^p,$$

where and $\Psi$ are sparsifying transforms chosen as wished, $\lambda$ and $\mu$ are tunable regularization parameters and p is 1 or 2, leading to a tractable equation.

(2) Train one or several networks N that take as input two images stacked in 2 different channels (or 4 channels in case of complex-valued images). The first image (x') is a clean image from a well-defined contrast A, the second image is an artifacted version of the corresponding image with well-defined contrast B. The network is then used at each iteration of an iterative CS reconstruction of the type:

$$\hat{x}^{t+1} = \operatorname*{argmin}_x \frac{1}{2}\|y - Ax\|_2^2 + \mu \|x - \bar{x}^t\|_2^2$$

$$\bar{x}^{t+1} = N(\hat{x}^{t+1}, x')$$

There can either be a single network N that is trained once, or as many networks as iterations to be performed, and the training is done end-to-end by minimizing the loss between the ground truth images x and the final estimate $\bar{x}^T$. This type of network training requires a paired training dataset.

(3) Both networks N described under the items (1) and (2) mentioned above can be made more flexible in their use if they are able to synthesize a range of different contrasts B starting from a range of different contrasts A. This allows to be robust to small changes of acquisition protocols that occur from scan to scan. The range of different contrasts A and B should be relatively narrow (small protocol changes around standard sequences of two reference contrasts A0 and B0). The network N then has one or several additional scalar inputs (s1, s2 ... sn) that are inputs to the first or to one or more of the following layers of N. At training, the vector s is varied along with the protocol changes. Once the network is trained, it can then produce different contrasts starting from a single input image x' by varying s to interpolate between contrasts.

(4) During the multi-contrast CS reconstruction, such a flexible network can be used in two ways. In a first use case, the exact protocol parameters are known and fed to the network through s, ensuring that the right contrast is produced. In a second use case, s is not known but estimated from the data. This can be done using a second network M, trained to infer s from outputs produced by N and retrospectively undersampled. In the MC-CS formulations described in items (1) and (2), a first step is added, producing an estimate $\hat{s} = M(A^T y)$, and that value is then used in N. Alternatively, a new estimate $\hat{s}^t = M(\hat{x}^t)$ could be produced at each iteration.

The methods described in items (1) and (2), also if augmented as described in (3), can be made robust to motion and/or varying resolution and FOV between the two contrasts by the use of rigid or non-rigid motion estimation and transformations, as done for example in some CS reconstructions with an additional time dimension. As for the method described in (3), this motion estimation can be performed once from the undersampled image $A^T y$ and the synthesized contrast N(x'), or at every iteration, as increasing quality of the estimate $\hat{x}^t$ allows increasing precision of the motion registration.

An application of the above examples is the acceleration of scanning protocols that contain acquisitions of the same anatomy with several different contrasts. The approach described here is limited to sequential reconstruction of the contrasts (as opposed to joint, simultaneous reconstruction of several undersampled contrasts), but can easily be extended to more than two contrasts and to joint reconstruction of the contrasts. An entire protocol can optimally be accelerated by starting with the acquisition of a "fast" contrast with high SNR, which is then used as reference contrast in the reconstruction of subsequent contrasts that are slower to acquire, but can be accelerated more thanks to MC-CS. The achievable acceleration rates using MC-CS are expected to be close to the acceleration rate achieved in dynamic CS (about a factor 2 higher than classical CS).

The issue of interscan motion can be handled as described in point (4) above. However, through-plane motion in multi-slice scans can be problematic in this aspect, therefore MC-CS would be particularly suited the sequences of 3D scans. Another way to reduce the motion problem would be to consider interleaved scans, which can also further reduce scan time. However, it should be noted that by shortening scanning time, MC-CS already helps to mitigate potential motion artifacts by a shorter overall scanning time, at the same time increasing patient comfort this way.

Example 1

In one possible implementation of variant (1), a contrast-to-contrast network is trained on paired or unpaired data of two well-defined contrasts A and B. The scanning protocol contains one sequence acquiring contrast A and one sequence acquiring contrast B, or a single sequence acquiring k-space profiles of both contrasts in an interleaved way. Contrast A is reconstructed first, using classical methods such as PI, CS or CS-PI, leading to a high quality image x'. This image x' is fed to the contrast-to-contrast network and produces an estimate $\bar{x}=N(x')\approx x$, where x is the image to be reconstructed for contrast B. Then, contrast B is reconstructed from the CS-undersampled k-space measured. The reconstruction uses and produces an estimate $$\hat{x} = \operatorname*{argmin}_{x} \frac{1}{2} \|y - Ax\|_2^2 + \lambda \|\Psi(x - \bar{x})\|_1$$

where $\Psi$ is a wavelet transform and $\lambda$ a tunable regularization parameter. As seen on FIG. 2, the obtained MC-CS reconstruction has far better image quality than the standard CS reconstruction.

Figure 7:
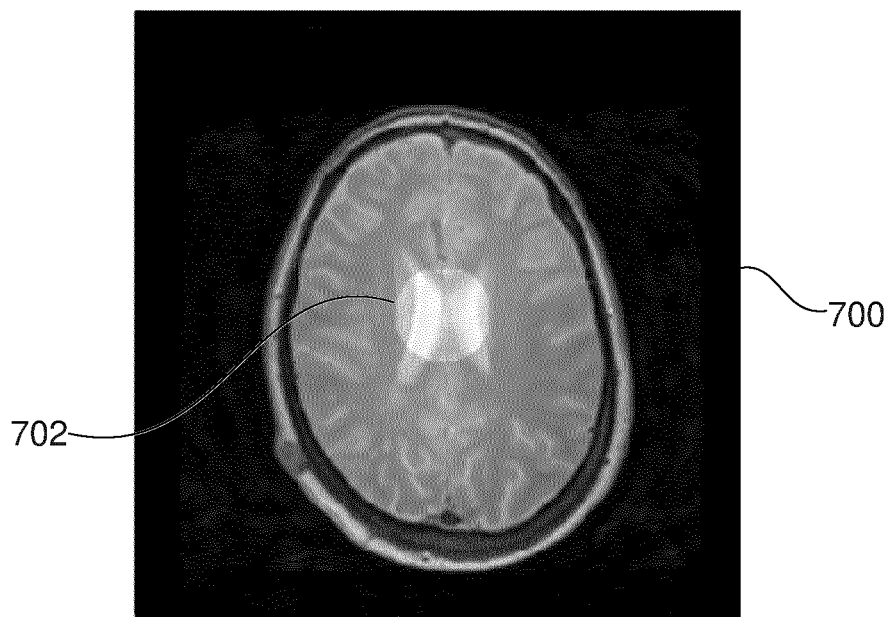
FIG. 7 shows an example of a fully sampled MR image.
Figure 8:
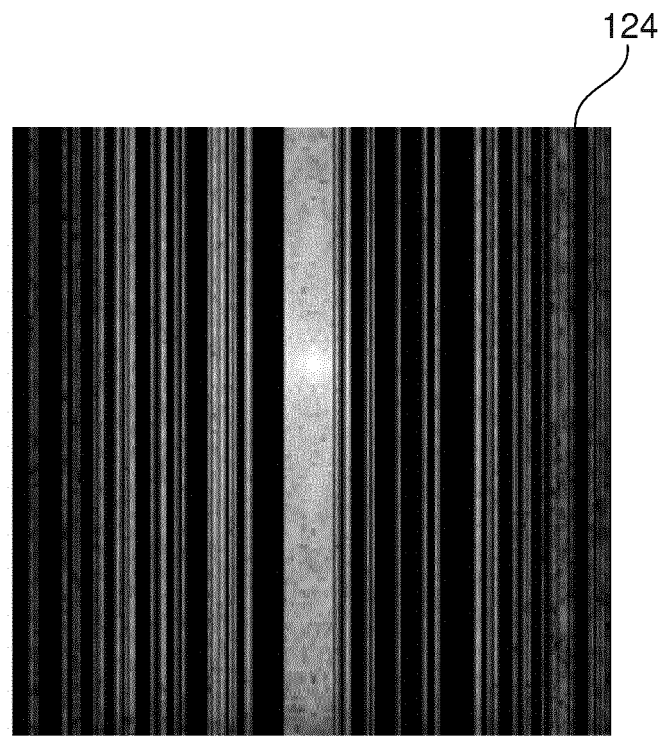
FIG. 8 shows an example of measured k-space data.

FIGS. 7-12 are used to illustrate the use of an image generating neural network 122 to assist in a compressed sensing reconstruction. In FIG. 7 a fully sampled image 700 is shown. For this example, a portion of the k-space data used to reconstruct image 700 is used. FIG. 8 shows an example of measured k-space data 124 that is undersampled. It is a portion of the k-spaced data used to reconstruct image 700 in FIG. 7.

Figure 9:
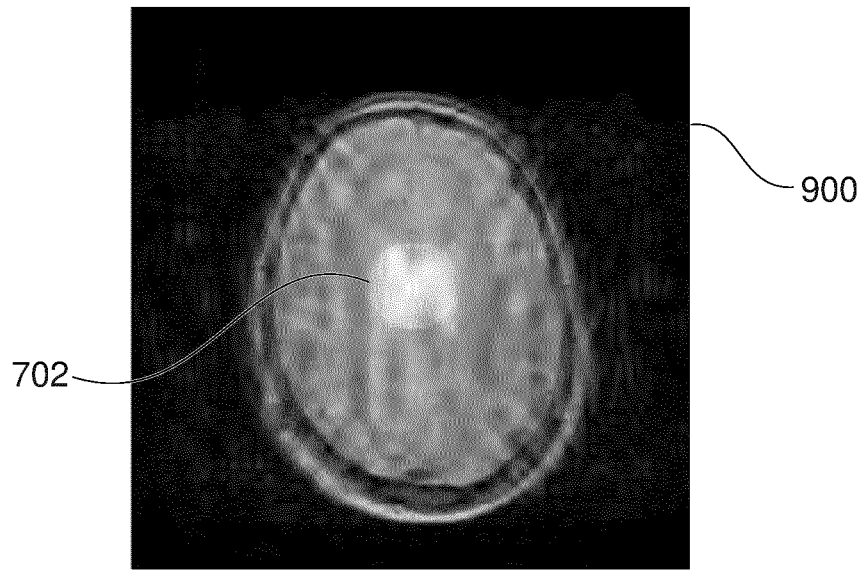
FIG. 9 shows a compressed sensing reconstruction of the measured k-space data of FIG. 8.
Figure 10:
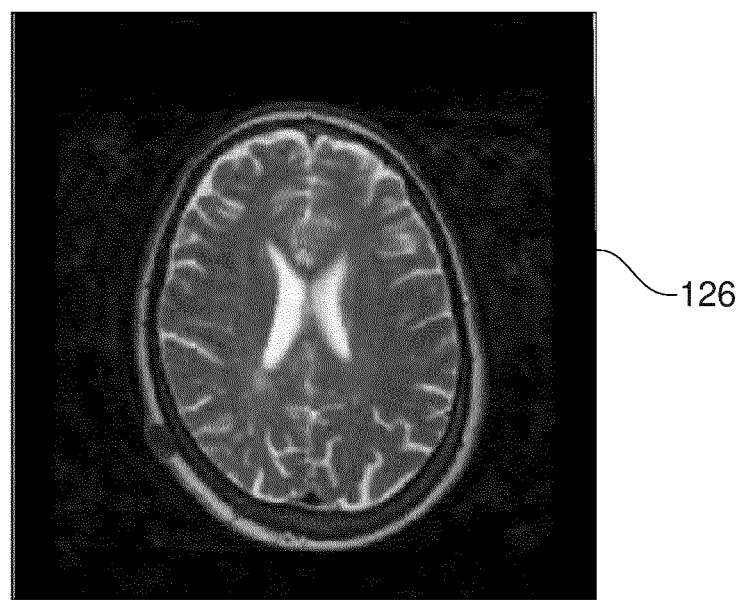
FIG. 10 shows an example of reference magnetic resonance image data.

FIG. 9 shows a wavelet compressed sensing reconstruction 900. It can be seen that the undersampled k-space data 124 in FIG. 8 was insufficient to reconstruct a quality image. FIG. 10 shows a different contrast or a reference magnetic resonance image data 126. Comparing images 700 and 126 it can be seen that the two images are of the same anatomy.

Figure 11:
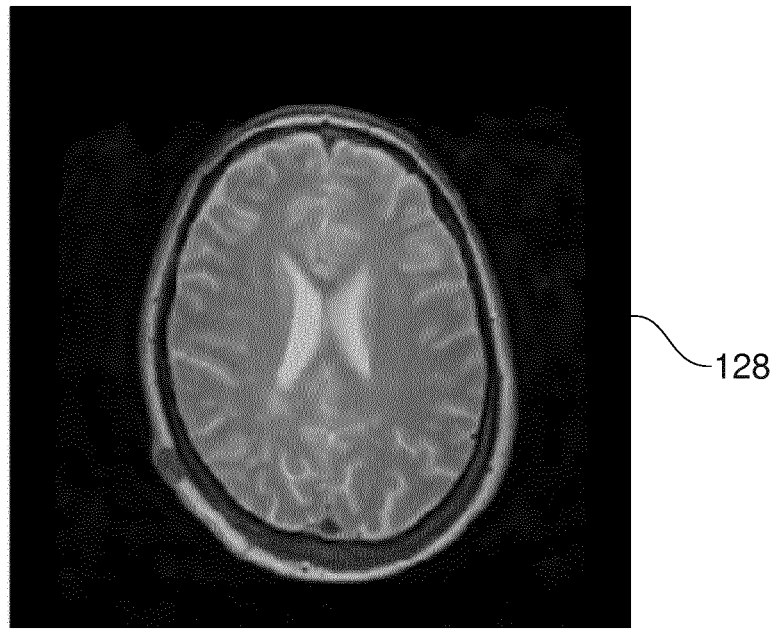
FIG. 11 shows and example of synthetic magnetic resonance image data 128.
Figure 12:
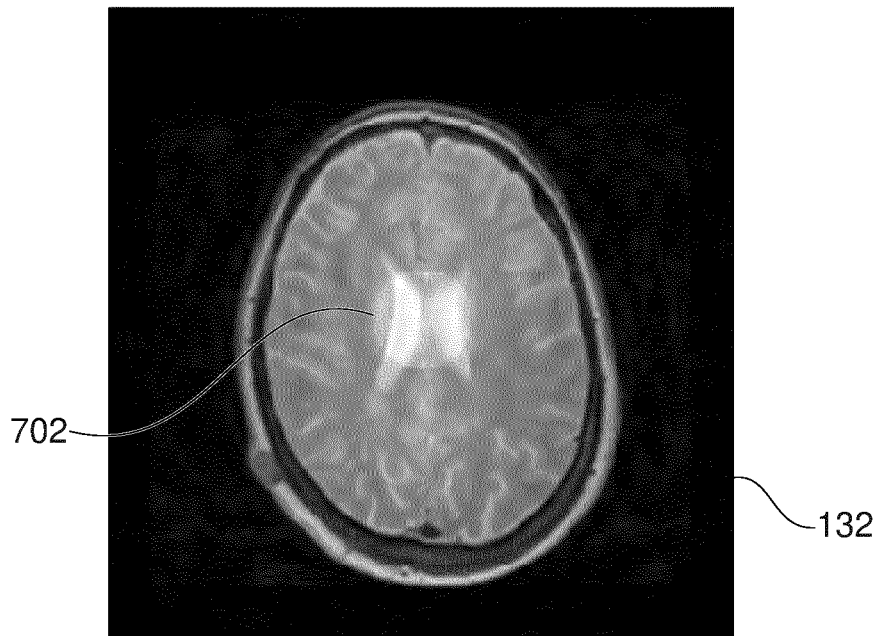
FIG. 12 shows and example of a corrected magnetic resonance image 132.

FIG. 11 shows an example of a synthetic magnetic resonance image data 128 that was generated from the reference magnetic resonance image data 126 using an image generating neural network 122. The synthetic magnetic resonance image data 128 is then used with the measured k-space data 124 of FIG. 8 to reconstruct the corrected magnetic resonance image data 132 depicted in FIG. 12. In this example the synthetic magnetic resonance image data 128 in FIG. 11 was used in the regularization term for the compressed sensing reconstruction.

In other words, FIGS. 7 to 12 are illustrations of MC-CS using a contrast-to-contrast network. FIGS. 7 and 10 are images representing the two contrasts A and B. The image of FIG. 10 is available from a previous scan, while FIG. 7 represents the image to be reconstructed from the measured undersampled k-space data shown in FIG. 8. FIG. 7 contains an artificially brightened central region 702 to illustrate the effect of the algorithm. Without the use of the reference contrast, the CS reconstruction shown in FIG. 9, using sparsity in a wavelet basis, still contains strong undersampling artifacts. In the proposed approach, a trained contrast-to-contrast network generates an estimate 128 show in in FIG. 11 of image 700 of FIG. 7, starting from FIG. 126. Using this estimate in the MC-CS reconstruction leads to FIG. 12, which has significantly improved image quality compared to FIG. 9. Structures that appear in FIG. 7 but not in FIG. 10 (the artificially central region 702 in the middle for example purpose) are preserved in the reconstruction of FIG. 12.

Example 2

The contrast-to-contrast networks used in method (1) as well as the different networks used in method (2) can have varying architectures. For example, they can be fully convolutional networks such as U-net or variants of it. In the case of (1), the training can be performed from a training dataset of unpaired images of contrasts A and B.

As an additional topic the use of an image generating neural network to reduce motion artifacts is discussed below. Image degradation due to subject motion during the acquisition is a persistent problem in the clinical application of magnetic resonance imaging (MRI). The associated artifacts typically appear as ghosting or blurring in the images and often reduce image quality to a degree that makes medical analysis impossible. In many cases, however, only a subset of all scans in an exam suffer from motion artifacts: many patients show varying motion activities during different parts of the exam. In addition, some MR sequences are more sensitive with respect to motion than others.

Many strategies for mitigation of motion artifacts in MR rely on the estimation of the underlying motion trajectory. This usually involves the application of a parametrized motion model, such as a rigid 3D model for brain scans. This can be problematic if the actual patient motion differs from this model, such as a swallowing motion in brain examinations. Alternatively, some parts of k-space can be rejected, and the missing data points are reconstructed using data redundancy of multi-coil acquisitions (i.e. SENSE-based reconstructions). This, however, necessarily involves a noise penalty.

The approach described in this invention disclosure avoids both drawbacks by leveraging information from a second artifact-free scan.

Application of the described invention is possible if multiple scans have been acquired in an exam, and if at least one of these scans is identified as being free of motion artifacts. Identification of this artifact-free scan may be performed manually by the operator, but it is also possible to automate this step using a dedicated metric, e.g. based on a neural network that is trained to estimate the motion artifact level in an image. The latter has been implemented and tested as part of a proof-of-concept (POC) study which is included below.

Figure 13:
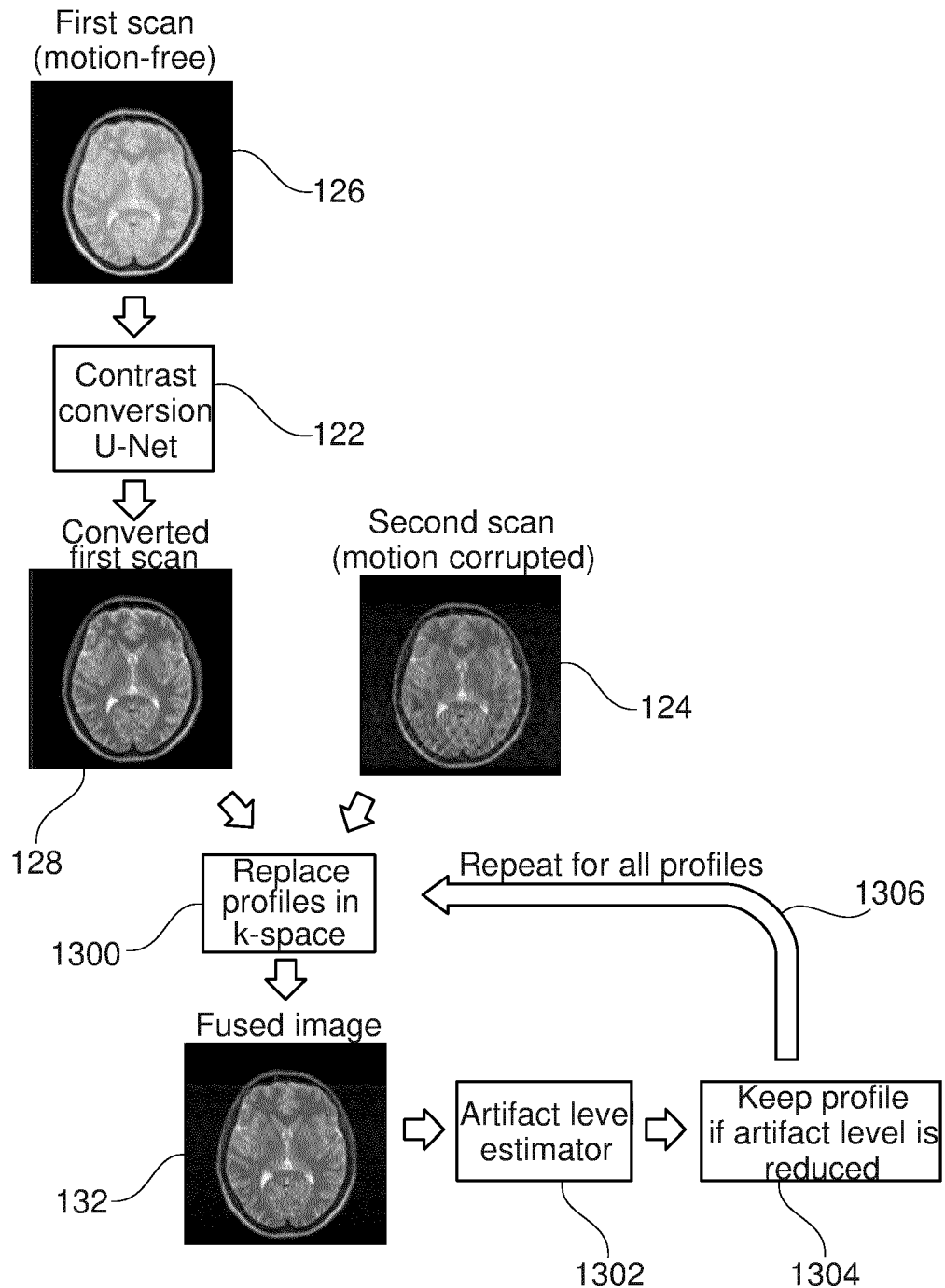
FIG. 13 illustrates an example method.

FIG. 13 illustrates a method of using the synthetic k-space data 130 to reduce motion artifacts in the corrected magnetic resonance image data 132. Block 126 represents the reference magnetic resonance image data, which in this case is a first scan that is motion free. Block 122 is a contrast-to-contrast conversion U-Net neural network which is equivalent to the image generating neural network 122. The output of this neural network 122 is the synthetic magnetic resonance image data 128, which is referred to as a converted first scan in this FIG. The second scan which is motion corrupted is equivalent to the measured k-space data 124. This is then used in an algorithm that replaces profiles in k-space 1300. The result is a corrected magnetic resonance image data 132. This can be performed multiple times. When this is performed multiple times the fused image 132 is an intermediate image. This is then input into the artifact level estimator 1302 or image quality estimation module. Block 1304 represents an algorithm step where the particular k-space profile that was replaced is kept if the artifact level is reduced. Step 1306 represents performing this iteratively for all profiles or for a certain number or a combination of k-space profiles.

In FIG. 13, assuming that a first scan (the reference magnetic resonance image data 126) in the exam is detected as free of motion artifacts, it is converted to the target contrast (synthetic magnetic resonance image data 128) using a dedicated contrast conversion network (image generating neural network 122). In a first POC study a U-Net architecture was used to realize this image translation module, but other architectures are possible as well. Creation of a suitable dataset can be realized in multiple ways:

Identify artifact-free scan pairs with identical geometry in a clinical database, create a database using registration of the two scans if necessary.

Acquire quantitative datasets that contain tissue parameter maps to enable forward simulation of arbitrary MR contrasts, i.e. proton density, T1 and T2 maps. Additional tissue parameters such as diffusion, perfusion etc. may be helpful to extend the method to functional MR sequences.

If matching scan pairs with identical geometry are not available, large datasets of (unpaired) scans may also be used. In this case, a cycleGAN network architecture can be used.

Using this trained contrast conversion network (image generating neural network 122), the first motion-free scan is then converted to the target contrast, i.e. the contrast of a second scan that is corrupted by motion artifacts. If the two scans do not have the same field-of-view and resolution, the first contrast can be brought to the second contrast's geometry by adjustment of the field of view and interpolation. If necessary, an image registration algorithm may be used to account for possible patient motion between the two scans. In all cases, a synthetic k-space of the contrast-converted, registered first scan is produced using the Fourier transform and the coil sensitivity maps.

To reduce the artifact level for this second scan, certain k-space profiles of the second scan are then replaced by the corresponding k-space profiles of the converted first scan. The selection of profiles for replacement depends on the type of scan and the specific k-space acquisition scheme: for a standard consecutive cartesian scheme, only a single profile can be replaced. For the POC study, where an interleaved TSE-like acquisition was assumed, all profiles corresponding to a single TSE shot were replaced (this corresponds to the assumption of negligible motion during each shot).

After each replacement of k-space profiles, the resulting "fused" dataset is Fourier transformed to obtain the fused image in image domain. The artifact level in the resulting fused image is estimated using a dedicated motion artifact level estimator. Different implementations of this module are possible, e.g. classical metrics such as total image gradient, image entropy, etc. In the POC study, a dedicated regression convolutional neural network (CNN) was trained to estimate the L2 norm of the artifacts in the image. Generation of the associated training dataset was realized based on motion-free volunteer T2w images as well as an artifact simulation pipeline. If the estimated artifact level in the fused image is considerably lower than the estimated artifact level in the original image, the profile(s) are considered to be corrupted by motion.

Once the entire k-space has been analyzed, the profiles that are considered to be corrupted are replaced by their counterparts in the converted motion-free dataset. A final Fourier transform and coil combination step then yields the artifact-corrected image.

Figure 14:
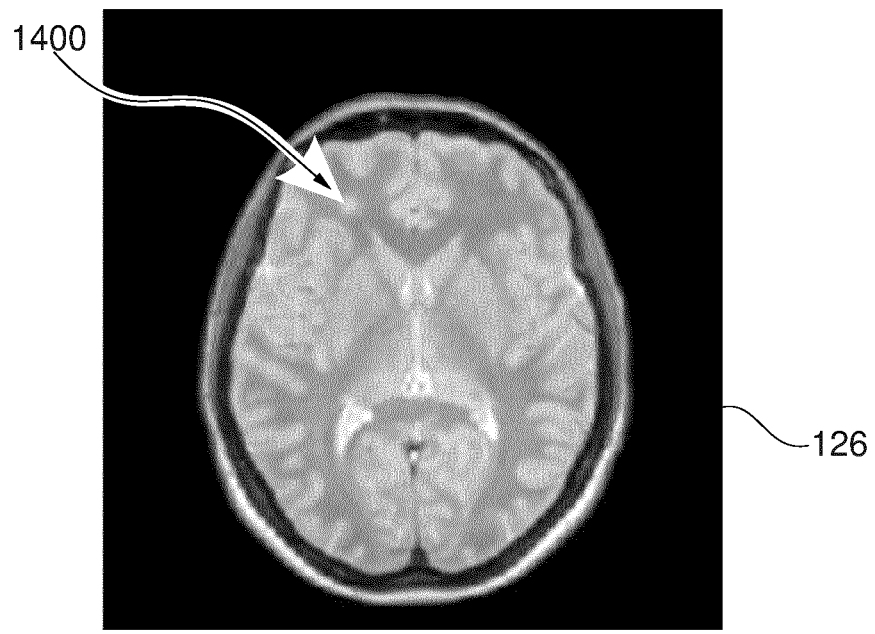
FIG. 14 shows an example of a reference magnetic resonance image data.
Figure 15:
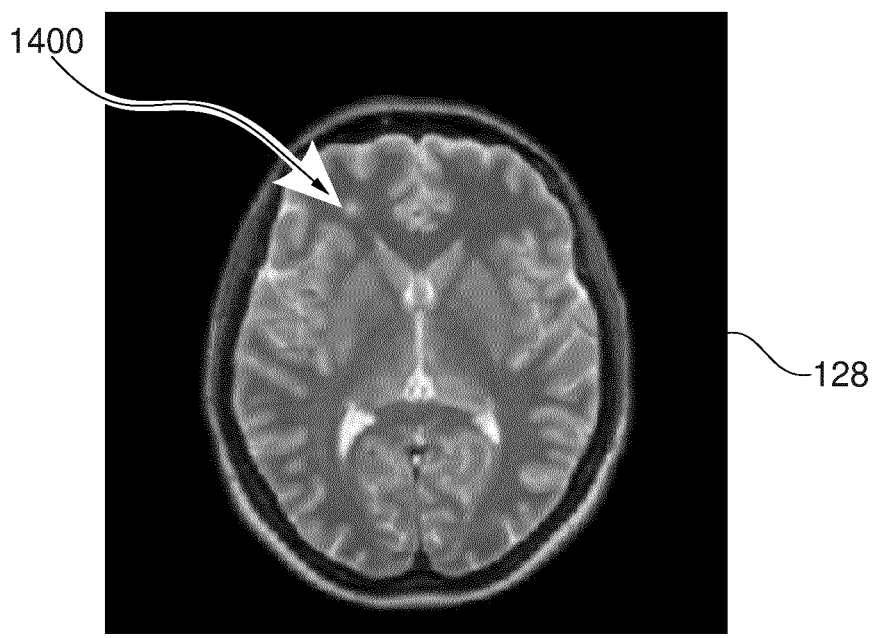
FIG. 15 shows an example of a synthetic magnetic resonance image data.
Figure 16:
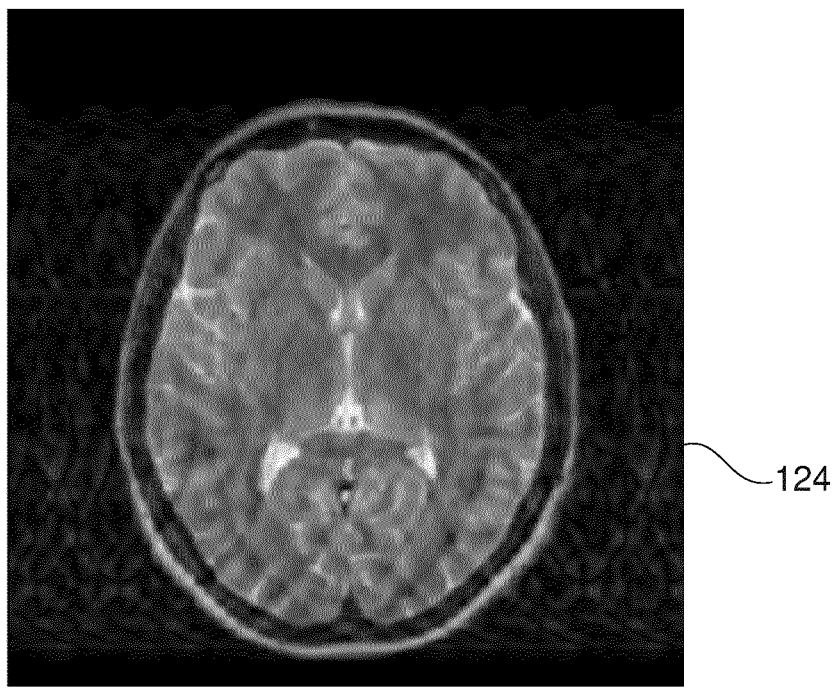
FIG. 16 shows a magnetic resonance image with motion artifacts caused by intentionally corrupting several lines of k-space data.
Figure 17:
FIG. 17 illustrates an example of a corrected magnetic resonance image data
Figure 18:
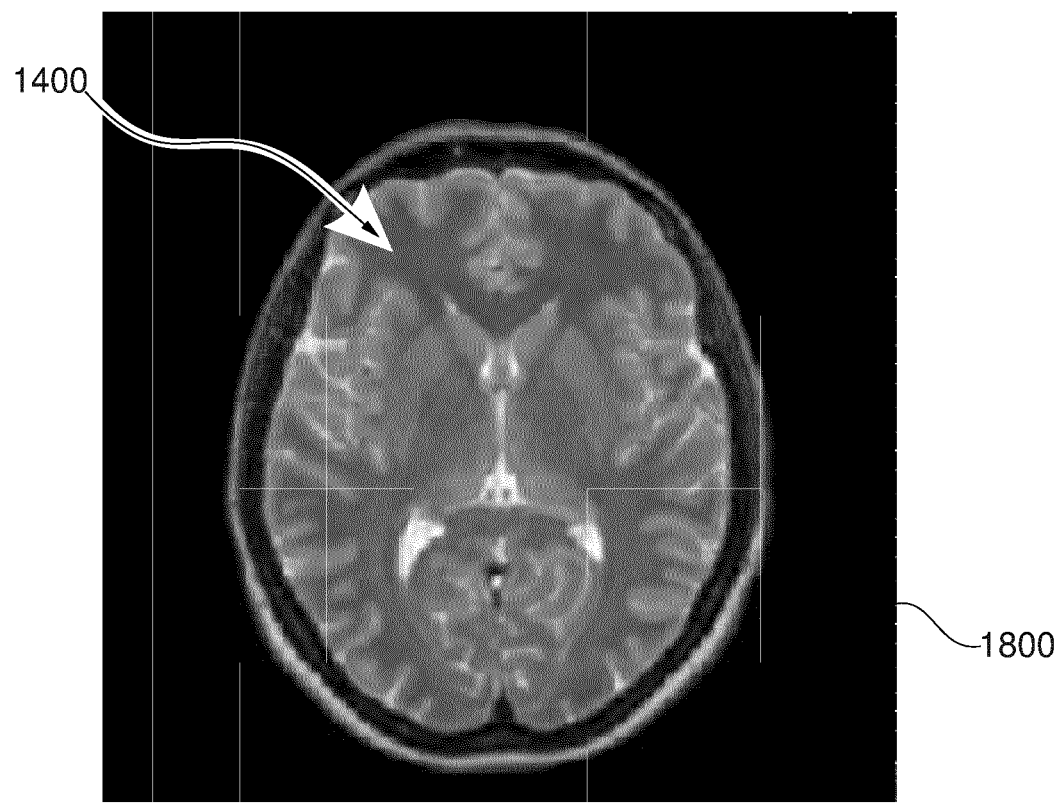
FIG. 18 shows a ground truth magnetic resonance image.

FIGS. 14-18 illustrate the effectiveness of the method illustrated in FIG. 13. FIG. 14 shows an example of a reference magnetic resonance image data 126 with a synthetic lesion 1400. FIG. 15 shows an example of a synthetic magnetic resonance image data 128 generated from image 126 in FIG. 14. FIG. 16 shows another magnetic resonance image with motion artifacts caused by intentionally corrupting several lines of k-space data. FIG. 17 illustrates an example of a corrected magnetic resonance image data 132 that was reconstructed using the method illustrated in FIG. 13 with the measured k-space data 124 of FIG. 16 and the synthetic magnetic resonance image data 128 that was used to replace some of the k-space data. This image is compared to FIG. 18 which shows a ground truth image 1800 which contains the same k-space data used to generate image 124 in FIG. 16 except that the k-space lines were not artificially corrupted. It can be shown that the images in FIGS. 17 and 18 show very good agreement.

In general, conversion between contrasts using a neural network cannot be expected to be completely error-free, as the underlying tissue properties are not entirely inferable from a single scan. As an illustrative example, a synthetic lesion was included in the first PD-weighted contrast in FIG. 14. This lesion is still visible in the result of the network-based contrast conversion, shown in FIG. 15. To demonstrate the robustness of the described method to errors during the contrast conversion process, the lesion was not included in the ground truth image of the second contrast (FIG. 18). Based on this ground truth image, the artifact-corrupted image in FIG. 16 was generated using forward simulation. Here, a TSE acquisition with 16 shots (256 profiles, TSE factor=16) was assumed, where two shots were corrupted by a 10° in-plane rotation.

Figure 19:
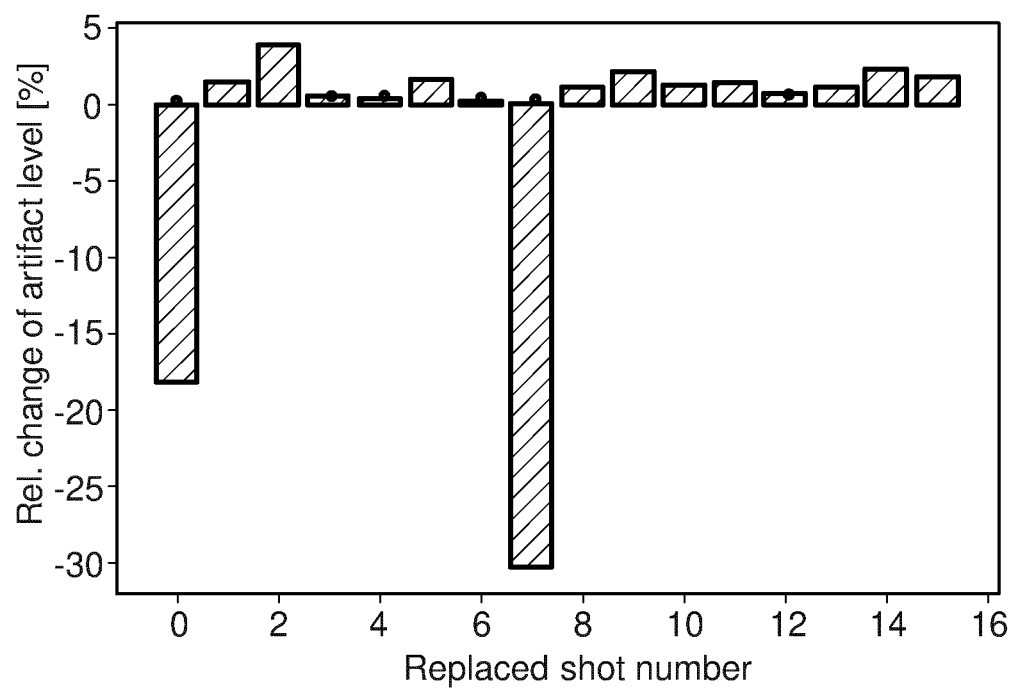
FIG. 19 shows the relative change of the estimated artifact level after replacement of the individual shots by the contrast-converted data shown in FIG. 15.

FIG. 19 below shows the relative change of the estimated artifact level after replacement of the individual shots by the contrast-converted data shown in FIG. 15. Shots #0 and #7 are correctly identified as motion-corrupted, as indicated by the large drop in estimated artifact level after replacement. Importantly, the synthetic lesion is not visible in the artifact-corrected result, shown in FIG. 17, even though two shots (=12.5%) in k-space were replaced by the converted data.

In general, the impact of replaced k-space lines on this "error propagation" will depend on the k-space trajectory, the number of replaced lines, etc. Empirical test can be easily performed to determine an upper limit for k-space replacement.

Further Features

For the design and application of the described examples, additional features can be considered:

To increase the accuracy of the contrast conversion, multiple scans can be used as input to the contrast conversion network, if available.

To avoid training of a dedicated contrast conversion network for each modification of the scan parameter settings (say, changes of TE and TR), the conversion network can be designed to incorporate these scan settings as additional inputs. One possibility for such a design is the inclusion of adaptive instance normalization (AdaIn) layers in the network.

Determination of the k-space locations affected by motion can be performed in advance, in order to avoid brute-force searching of the locations responsible for the corruption. This determination can for example be made with the use of external sensors (respiratory belt, in-bore camera) that track patient motion over time, or with methods exploiting raw data inconsistencies, which is possible thanks to the data redundancy in multi-coil scans.

The applicability of the method is not reduced to Cartesian scans and is valid for any combination of k-space trajectories.

Figure 20:
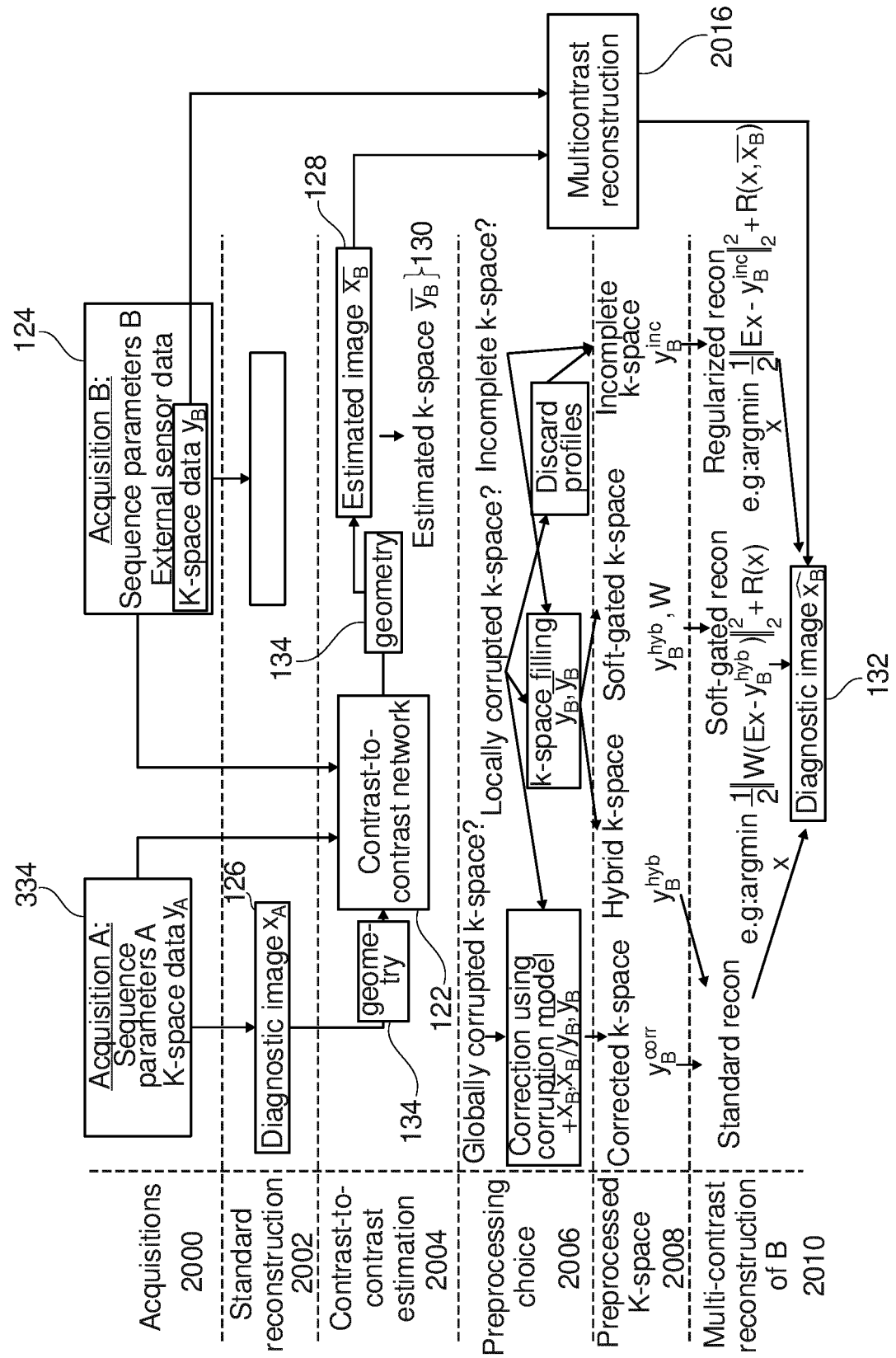
FIG. 20 shows a flowchart which illustrates a variety of ways of reconstructing the corrected magnetic resonance image data.

FIG. 20 shows a flowchart which illustrates a variety of ways of reconstructing the corrected magnetic resonance image data 132. The steps are divided into several major steps. Step 2000 represents the acquisitions of the measured k-space data 124 and the reference k-space data 334. In the next step standard reconstructions 2002 are performed. In this step an unused or corrupted image may be reconstructed directly from the measured k-space data 124, however this is not used in this method. The reference magnetic resonance image data 126 is reconstructed from the reference k-space data 334. The image 126 is then input into the image generating neural network 122 or contrast-to-contrast network to produce the estimated image or synthetic magnetic resonance image data 128. Before inputting the reference magnetic resonance image data 126 into the neural network 122 there may be a geometry modification using a geometry modification module 134. Likewise, after the data is output of the neural network 122, the estimated image or synthetic magnetic resonance image data 128 may have its form altered by a geometry correction using a geometry modification module 134. The estimated image 128 may also be used to generate the estimated k-space data or synthetic k-space data 130. The steps in level 2006 represent several different pre-processing choices.

For example, there may be globally corrupted k-space in which case there is a correction model which may be used. For example, in an EPI magnetic resonance image acquisition the even and odd echoes may be shifted. The estimated k-space data may be used to detect and correct this. Another pre-processing choice may be locally corrupted k-space data. For example, if there was an error the k-space data could be discarded and simply filled as was illustrated in FIG. 13. Another pre-processing choice would be incomplete k-space. In this example you may have a choice of either proceed with an incomplete k-space or performing k-space filling. Depending upon the pre-processing choice taken in step 2006, there may also be some pre-processed k-space 2008.

In another example, corrected k-space data may be generated as a hybrid k-space which is a combination of both the estimated k-space 130 and the actually acquired k-space 124. The k-space may also be so called soft gated, where replaced k-space data is given a lower weighting factor so it has less influence on the final image. In another example the image may be reconstructed with an incomplete k-space or simply the profiles are discarded. Step 2010 represents the multi-contrast reconstruction to generate the diagnostic image 132. This results in using a standard reconstruction if the corrected k-space or hybrid k-space is used, a soft gated reconstruction if the soft gated weighting is used or, if there is incomplete k-space, the estimated image 128 may be used as a regularization term.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 computer
104 hardware interface
106 computational system
108 user interface
110 memory
120 machine executable instructions
122 image generating neural network
124 measured k-space data
126 reference magnetic resonance image data
128 synthetic magnetic resonance image data
130 synthetic k-space data
132 corrected magnetic resonance image data
134 image processing module
200 receive measured k-space data acquired according to the first configuration of the magnetic resonance imaging system
202 receive the reference magnetic resonance image data, wherein the reference magnetic resonance image data is descriptive of the region of interest of the subject
204 receive the synthetic magnetic resonance image data by inputting the reference magnetic resonance image data into the image generating neural network
206 reconstruct corrected magnetic resonance image data from the measured k-space data and the synthetic magnetic resonance image data
300 medical system
302 magnetic resonance imaging system
304 magnet
306 bore of magnet
308 imaging zone 309 region of interest
310 magnetic field gradient coils
312 magnetic field gradient coil power supply
314 radio-frequency coil
316 transceiver
318 subject
320 subject support
330 first pulse sequence commands
332 second pulse sequence commands
334 reference k-space data
400 acquire the reference k-space data by controlling the magnetic resonance imaging system with the second pulse sequence commands
402 reconstruct the reference magnetic resonance image data from the reference k-space data
404 acquire the measured k-space data by controlling the magnetic resonance imaging system with the first pulse sequence command
500 magnetic resonance imaging system
502 corrected magnetic resonance image
600 acquire the reference k-space data by controlling the magnetic resonance imaging system with the second pulse sequence commands
602 reconstruct the reference magnetic resonance image data from the reference k-space data
604 receive the synthetic magnetic resonance image data by inputting the reference magnetic resonance image data into the image generating neural network
606 construct synthetic k-space data using the synthetic magnetic resonance image data
608 control acquisition of the measured k-spaced data using the first pulse sequence commands and the synthetic k-space data
700 fully sampled image
900 wavelet reconstructed image
1300 image quality estimation module
1400 synthetic lesion
1800 ground truth image
2000 acquisitions
2002 standard reconstruction
2004 contrast-to-contrast estimation
2006 preprocessing choice
2008 preprocessed k-space
2010 multi-contrast reconstruction of B
2016 multi-contrast reconstruction

The invention claimed is:

1. A medical system comprising:
a memory storing machine executable instructions and access to an image generating neural network, wherein the image generating neural network is configured for outputting synthetic magnetic resonance image data in response to receiving reference magnetic resonance image data as input, wherein the image generating neural network is configured to generate the synthetic magnetic resonance image data as a simulation of magnetic resonance image data acquired according to a first configuration of a magnetic resonance imaging system when the reference magnetic resonance image data is acquired according to a second configuration of the magnetic resonance imaging system;
a computational system configured to control the medical system, wherein execution of the machine executable instructions causes the computational system to:
access measured k-space data acquired according to the first configuration of the magnetic resonance imaging system, wherein the measured k-space data is descriptive of a region of interest of a subject;
access the reference magnetic resonance image data, wherein the reference magnetic resonance image data is descriptive of the region of interest of the subject;
generate access to the synthetic magnetic resonance image data by inputting the reference magnetic resonance image data into the image generating neural network; and
arrange to reconstruct corrected magnetic resonance image data from the measured k-space data and the synthetic magnetic resonance image data.

2. The medical system of claim 1, wherein the synthetic magnetic resonance image data provides prior knowledge during the reconstruction of the corrected magnetic resonance image data.

3. The medical system of claim 1, wherein execution of the machine executable instructions further causes the computational system to reconstruct synthetic k-space data from the synthetic magnetic resonance image data, wherein the measured k-space data is divided into groups of k-space data, wherein the corrected magnetic resonance image data is reconstructed by using the synthetic k-space data to modify at least a portion of the groups of k-space data.

4. The medical system of claim 3, wherein execution of the machine executable instructions further causes the computational system to:
use the synthetic k-space data to determine a rigid body transformation of one or more of the groups of k-space data; and
perform a phase and amplitude correction of the one or more of the groups of k-space data using the rigid body transformation.

5. The medical system of claim 3, wherein execution of the machine executable instructions further causes the computational system to:
detect at least one incomplete k-space sampling region in the measured k-space data; and
fill the incomplete k-space sampling region in the measured k-space data with the synthetic k-space data.

6. The medical system of claim 3, wherein the memory further contains an image quality evaluation module configured for outputting an image quality metric, wherein execution of the machine executable instructions further causes the computational system to:
generate multiple k-space data sets by systematically replacing combinations of the groups of k-space data with portions of the synthetic k-space data;
generate multiple trial magnetic resonance image data by reconstructing each of the multiple k-space data sets; and
select the corrected magnetic resonance image data from the multiple trial magnetic resonance image data by optimizing the image quality metric output by the image quality evaluation module.

7. The medical system of claim 3, wherein the reconstruction of the corrected magnetic resonance image data from the measured k-space data and the synthetic magnetic resonance image data is formulated an optimization problem that assigns weighting factors to each of the groups of k-space data, wherein execution of the machine executable instructions further causes the computational system to:
identify at least one corrupted group of k-space data selected from the groups of k-space data; and
correct the at least one corrupted group of k-space data using the synthetic k-space data;

assign the weighting factors for each of the groups of k-space data, wherein the at least one corrupted group of k-space data is assigned a reduced value weighting factor.

8. The medical system of claim 1, wherein the corrected magnetic resonance image data is reconstructed according to a compressed sensing image reconstruction algorithm, wherein the compressed sensing image reconstruction algorithm is an iterative algorithm that generates an intermediate magnetic resonance image repeatedly, wherein the compressed sensing image reconstruction algorithm comprises denoising the intermediate magnetic resonance image using the synthetic magnetic resonance image data.

9. The medical system of claim 1, wherein the medical system further comprise at least one magnetic resonance imaging system, wherein the memory further contains first pulse sequence commands configured to control the at least one magnetic resonance imaging system to acquire the measured k-space data, wherein the memory further contains second pulse sequence commands configured to control the at least one magnetic resonance imaging system to acquire reference k-space data, wherein execution of the machine executable instructions further causes the computational system to:
 acquire the reference k-space data by controlling the magnetic resonance imaging system with the second pulse sequence commands;
 reconstruct the reference magnetic resonance image data from the reference k-space data; and
 acquire the measured k-space data by controlling the magnetic resonance imaging system with the first pulse sequence command.

10. The medical system of claim 9, wherein execution of the machine executable instructions further causes the computational system to:
 construct synthetic k-space data using the synthetic magnetic resonance image data; and
 control acquisition of the measured k-spaced data using the synthetic k-space data.

11. The medical system of claim 10, wherein execution of the machine executable instructions causes the computational system to control the acquisition of the measured k-space data by choosing a k-space sampling pattern for the first pulse sequence commands using the synthetic k-space data.

12. The medical system of claim 10, wherein the first pulse sequence commands are configured to control the magnetic resonance imaging system to acquire the measured k-space data in groups of k-space data, wherein execution of the machine executable instructions further causes the computational system to:
 calculate a comparison metric between the synthetic k-space data and each of the groups of k-space data; and
 perform a predetermined action if the comparison metric is outside of a predetermined value range.

13. The medical system of claim 1, wherein the corrected magnetic resonance image data is reconstructed according to a parallel imaging magnetic resonance imaging reconstruction algorithm.

14. A computer program comprising machine executable instructions stored on a non-transitory computer readable medium for execution by a computational system, wherein the computer program further comprises an image generating neural network configured for outputting synthetic magnetic resonance image data in response to receiving reference magnetic resonance image data as input, wherein the image generating neural network is configured to generate the synthetic magnetic resonance image data as a simulation of magnetic resonance image data acquired according to a first configuration of a magnetic resonance imaging system when the reference magnetic resonance image data is acquired according to a second configuration of the magnetic resonance imaging system, wherein execution of the machine executable instructions causes the computational system to:
 access the measured k-space data acquired according to the first configuration of the magnetic resonance imaging system, wherein the measured k-space data is descriptive of a region of interest of a subject;
 access the reference magnetic resonance image data, wherein the reference magnetic resonance image data is descriptive of the region of interest of the subject;
 generate access the synthetic magnetic resonance image data by inputting the reference magnetic resonance image data into the image generating neural network; and
 arrange to reconstruct corrected magnetic resonance image data from the measured k-space data and the synthetic magnetic resonance image data.

15. A magnetic resonance imaging system, wherein the magnetic resonance imaging system comprises:
 a memory configured to store machine executable instructions and an image generating neural network, wherein the image generating neural network in configured for outputting synthetic magnetic resonance image data in response to receiving a reference magnetic resonance image data as input, wherein the image generating neural network is configured to generate the synthetic magnetic resonance image data as a simulation of a magnetic resonance image data acquired according to a first configuration of a magnetic resonance imaging system when the reference magnetic resonance image data is acquired according to a second configuration of the magnetic resonance imaging system, wherein the memory further contains first pulse sequence commands configured to control the magnetic resonance imaging system to acquire the measured k-space data, wherein the memory further contains second pulse sequence commands configured to control the magnetic resonance imaging system to acquire reference k-space data;
 a computational system, wherein execution of the machine executable instructions causes the computational system to:
 acquire the reference k-space data by controlling the magnetic resonance imaging system with the second pulse sequence commands;
 arrange to reconstruct the reference magnetic resonance image data from the reference k-space data;
 access the synthetic magnetic resonance image data by inputting the reference magnetic resonance image data into the image generating neural network;
 arrange to construct synthetic k-space data+using the synthetic magnetic resonance image data; and
 control acquisition of the measured k-spaced data using the first pulse sequence commands and the synthetic k-space data.

* * * * *